United States Patent
Hirose

(10) Patent No.: US 8,279,057 B2
(45) Date of Patent: Oct. 2, 2012

(54) METHOD OF DETECTING PRESENCE OF SUBJECT ON BED

(75) Inventor: Kazuo Hirose, Oyama (JP)

(73) Assignee: Showa Denko K.K., Tokyo (JP)

( * ) Notice: Subject to any disclaimer, the term of this patent is extended or adjusted under 35 U.S.C. 154(b) by 432 days.

(21) Appl. No.: 12/305,778

(22) PCT Filed: Jun. 18, 2007

(86) PCT No.: PCT/JP2007/062202
§ 371 (c)(1),
(2), (4) Date: May 28, 2010

(87) PCT Pub. No.: WO2007/148638
PCT Pub. Date: Dec. 27, 2007

(65) Prior Publication Data
US 2010/0231376 A1 Sep. 16, 2010

(30) Foreign Application Priority Data
Jun. 19, 2006 (JP) ................. 2006-168484

(51) Int. Cl.
*G08B 23/00* (2006.01)
(52) U.S. Cl. ........ 340/517; 340/533; 340/595; 340/620; 340/604; 340/665; 340/666; 340/539.16; 340/573.1; 340/573.4; 600/534; 600/595; 5/600; 5/611; 5/616; 5/618; 5/620
(58) Field of Classification Search ........... 340/517, 340/533, 620, 595, 604, 665, 666, 539.16, 340/573.1, 573.4; 600/534, 595; 5/600, 5/611, 616, 618, 620
See application file for complete search history.

(56) References Cited

U.S. PATENT DOCUMENTS

| 5,410,297 | A  | * | 4/1995  | Joseph et al. ........... 340/573.7 |
| 6,067,019 | A  | * | 5/2000  | Scott ..................... 340/573.4 |
| 6,778,090 | B2 | * | 8/2004  | Newham .................. 340/573.1 |
| 7,652,581 | B2 | * | 1/2010  | Gentry et al. .......... 340/573.1 |
| 2006/0028350 | A1 | | 2/2006  | Bhai |
| 2007/0235036 | A1 | | 10/2007 | Bobey et al. |
| 2007/0268147 | A1 | | 11/2007 | Bhai |

FOREIGN PATENT DOCUMENTS

JP  59 45085   11/1984
JP  8 80286    3/1996
(Continued)

OTHER PUBLICATIONS

Office Action issued Feb. 8, 2012, in Japanese Patent Application No. 2008-522441 with English translation.

(Continued)

*Primary Examiner* — Tai T Nguyen
(74) *Attorney, Agent, or Firm* — Oblon, Spivak, McClelland, Maier & Neustadt, L.L.P.

(57) ABSTRACT

A bed occupancy state detection method includes detecting loads applied to a head side right portion, a head side left portion, a foot side right portion, and a foot side left portion of a bed platform by first to fourth load detecters, respectively, judging whether or not a prescribed judgment formula is satisfied based on load values outputted from the first to fourth load detecters, and notifying information on a bed occupancy state of an object in cases where it is judged that a judgment formula is satisfied from a judgment result at the judgment.

23 Claims, 9 Drawing Sheets

FOREIGN PATENT DOCUMENTS

| | | |
|---|---|---|
| JP | 2000-105884 | 4/2000 |
| JP | 3093745 | 10/2000 |
| JP | 2000-316915 | 11/2000 |
| JP | 2000-325409 | 11/2000 |
| JP | 3322632 | 9/2002 |
| JP | 2006 30120 | 2/2006 |
| WO | WO 2005/107674 A2 | 11/2005 |
| WO | WO 2005/107674 A3 | 11/2005 |

OTHER PUBLICATIONS

Extended European Search Report issued Dec. 16, 2010, in application No. 07745452.8-1257 / 2030601 PCT/JP2007062202.

* cited by examiner

METHOD OF DETECTING PRESENCE OF SUBJECT ON BED

TECHNICAL FIELD

The present invention relates to a bed occupancy state detection method for detecting, e.g., a bed occupancy state of a subject on a bed platform (e.g., a state in which a subject is not on a bed, a state in which a subject is on a bed, subject's body movements on a bed), a bed occupancy state detection device, and a bed occupancy state detection method.

BACKGROUND ART

For detecting a bed occupancy state, such as, e.g., a state in which a subject (e.g., a patient, an aged person, a care recipient, a healthy person, or a baby) on a bed platform is getting out of a bed, a state in which a subject is getting onto a bed, or a position of the center of gravity of a subject, the following method is known for example.

First to fourth load detectors are disposed under the head side right leg portion, the head side left leg portion, the foot side right leg portion, and the foot side left leg portion of a bed, respectively. These four load detectors detect the loads applied to the head side right portion of the bed platform, the head side left portion thereof, the foot side right portion thereof, and the foot side left portion thereof. Using the outputted loads (load values) from these four load detectors, the gravity center of the subject on the bed platform is calculated. The coordinate (GX, GY) of the center of gravity of the object can be calculated from the following formulas (101) and (102).

$$GX = (W1 + W2 - W3 - W4) \times (1/WT) \times (BX/2) \quad \text{Formula (101)}$$

$$GY = (W1 + W3 - W2 - W4) \times (1/WT) \times (BY/2) \quad \text{Formula (102)}$$

where,
W1: output load (load value) from the first load detector
W2: output load (load value) from the second load detector
W3: output load (load value) from the third load detector
W4: output load (load value) from the fourth load detector
BX: distance between the leg portions of the bed in the length direction (i.e., in the X-axis direction)
BY: distance between the leg portions of the bed in the width direction (i.e., in the Y-axis)

$$WT = W1 + W2 + W3 + W4$$

Based on the position of the center of gravity calculated by these gravity center position formulas (101) and (102), the moving direction, the moving speed, etc., of the subject on the bed platform are calculated. From the calculated results, the bed occupancy state of the subject will be detected (see, e.g., Patent Documents 1 and 2).

In the meantime, if values corresponding to lying postures of a subject on a bed platform is detected, it is useful on the following points. That is, for example, the detection enables prediction of the subject's getting out of the bed or prediction of the possibility of the subject's falling down from the bed platform. Therefore, it is important to detect values corresponding to the lying postures of a subject.

Patent Document 1: Japanese Patent Publication No. 3,322,632
Patent Document 2: Japanese Patent Publication No. 3,093,745

DISCLOSURE OF THE INVENTION

Problems to be Solved by the Invention

In the aforementioned conventional detection method, however, the subject's bed occupancy state is detected based on the center of gravity of the subject calculated by the aforementioned formulas (101) (102) using the outputted loads from the four load detectors. Therefore, in some cases, depending on the type of the lying posture of the subject, the value corresponding to the lying posture cannot be detected.

The preferred embodiments of the present invention have been developed in view of the above-mentioned and/or other problems in the related art. The preferred embodiments of the present invention can significantly improve upon existing methods and/or apparatuses.

The present invention was made in view of the aforementioned technical background, and aims to provide a bed occupancy state detection method capable of detecting values corresponding to various lying postures of an object, a bed occupancy state detection apparatus for use in the detection method, and a bed occupancy state monitoring system using the detection apparatus.

Other purposes and advantages of the present invention will be apparent from the following preferred embodiments.

Means for Solving the Problems

The present invention provides the following means.

[1] A bed occupancy state detection method, comprising:
a load detection step for detecting loads applied to a head side right portion, a head side left portion, a foot side right portion, and a foot side left portion of a bed platform by first to fourth load detection means, respectively;
wherein load values outputted form the first to fourth load detection means are defined as W1, W2, W3, and W4, respectively,
a first judgment step for judging whether or not a first judgment formula (1) is satisfied, wherein the first judgment formula (1) is given by $W1/(W1+W3) \leq n1$, where $0 < n1 < 0.5$ (n1: previously set value);
a second judgment step for judging whether or not a second judgment formula (2) is satisfied, wherein the second judgment formula (2) is given by $W1/(W1+W3) \geq n2$, where $0.5 < n2 < 1$ (n2: previously set value);
a third judgment step for judging whether or not a third judgment formula (3) is satisfied, wherein the third judgment formula (3) is given by $W2/(W2+W4) \leq n3$, where $0 < n3 < 0.5$ (n3: previously set value);
a fourth judgment step for judging whether or not a fourth judgment formula (4) is satisfied, wherein the fourth judgment formula (4) is given by $W2/(W2+W4) \geq n4$, where $0.5 < n4 < 1$ (n4: previously set value);
a fifth judgment step for judging whether or not a fifth judgment formula (5) is satisfied, wherein the fifth judgment formula (5) is given by $W1/(W1+W2) \leq n5$, where $0 < n5 < 0.5$ (n5: previously set value);
a sixth judgment step for judging whether or not a sixth judgment formula (6) is satisfied, wherein the sixth judgment formula (6) is given by $W1/(W1+W2) \geq n6$, where $0.5 < n6 < 1$ (n6: previously set value);
a seventh judgment step for judging whether or not a seventh judgment formula (7) is satisfied, wherein the seventh judgment formula (7) is given by $W3/(W3+W4) \leq n7$, where $0 < n7 < 0.5$ (n7: previously set value);
an eighth judgment step for judging whether or not an eighth judgment formula (8) is satisfied, wherein the eighth judgment formula (8) is given by $W3/(W3+W4) \geq n8$, where $0.5 < n8 < 1$ (n8: previously set value); and
a first notification step for notifying information on a bed occupancy state of an object when it is judged that at least one judgment formula is satisfied from a judgment result of at least one judgment step among the first to eighth judgment steps.

[2] The bed occupancy state detection method as recited in Item 1, further comprising a first communication step for transmitting information on the bed occupancy state of the object when it is judged that the judgment formula is satisfied from the judgment result of the at least one judgment step.

[3] The bed occupancy state detection method as recited in Item 1 or 2, wherein the information on the bed occupancy state of the object is information that an occupancy position of the object is in an end region of the bed platform.

[4] The bed occupancy state detection method as recited in any one of Items 1 to 3, further comprising:

a total load value calculation step for calculating a total load value A which is a sum of four load values outputted from the first to fourth load detection means;

a total load value storage step for storing the total load value A calculated at the total load value calculation step;

a bed occupancy state judgment step for judging whether or not the object has been on the bed platform depending on whether or not the total load value A calculated at the total load value calculation step has maintained the predetermined load value or more for a predetermined time period;

an occupancy load value storage step of storing the total load value at the time when the predetermined time period has passed as an occupancy load value B in a state in which the object is on the bed platform when it is judged that the object has been on the bed platform from the judgment result of the bed occupancy state judgment step;

a ninth judgment step for judging whether or not a ninth judgment formula (9) is satisfied, wherein the ninth judgment formula (9) is given by $A \leqq B \times m1$, where $0 < m1 < 1$ (m1: previously set value); and when it is judged that the ninth judgment formula is satisfied from a judgment result of the ninth judgment step, further comprising, a tenth judgment step for judging whether or not a tenth judgment formula (10) is satisfied, wherein the tenth judgment formula (10) is given by $A < B \times m2$, where $0 < m2 < m1$ (m2: previously set value); and a second notification step for notifying information that the object has got out of the bed when it is judged that the tenth judgment formula is satisfied from the judgment result of the tenth judgment step.

[5] The bed occupancy state detection method as recited in Item 4, further comprising a second communicating step for transmitting information that the object has got out of the bed when it is judged that the tenth judgment formula is satisfied from the judgment result of the tenth judgment step.

[6] The bed occupancy state detection method as recited in any one of Items 1 to 3, further comprising:

a total load value calculation step for calculating a total load value A which is a sum of four load values outputted from the first to fourth load detection means;

a total load value storage step for storing the total load value A calculated at the total load value calculation step;

a bed occupancy state judgment step for judging whether or not the object has been on the bed platform depending on whether or not the total load value A calculated at the total load value calculation step has maintained a predetermined load value or more for a predetermined time period;

an occupancy load value storage step of storing the total load value at the time when the predetermined time period has passed as an occupancy load value B in a state in which the object is on the bed platform when it is judged that the object has been on the bed platform from the judgment result of the bed occupancy state judgment step;

a maximum and minimum load value calculation step for calculating a maximum total load value Amax and a minimum total load value Amin of the total load value A calculated at the total load value calculation step within a predetermined time period;

an eleventh judgment step for judging whether or not an eleventh judgment formula (11) is satisfied, wherein the eleventh judgment formula (11) is given by $Amax - Amin \geqq B \times q$, where $0 < q$ (q: previously set value); and a third notification step for notifying information on body movements of the object when it is judged that the eleventh judgment formula is satisfied from the judgment result of the eleventh judgment step.

[7] The bed occupancy state detection method as recited in Item 6, further comprising a third communicating step for transmitting information on body movements of the object when it is judged that the eleventh judgment formula is satisfied from the judgment result of the eleventh judgment step.

[8] The bed occupancy state detection method as recited in any one of Items 1 to 3, further comprising:

a total load value calculation step for calculating a total load value A which is a sum of four load values outputted from the first to fourth load detection means;

a total load value storage step for storing the total load value A calculated at the total load value calculation step;

a bed occupancy state judgment step for judging whether or not the object has been on the bed platform depending on whether or not the total load value A calculated at the total load value calculation step has maintained a predetermined load value or more for a predetermined time period;

a head side load value calculation step for calculating a head side load value C which is a sum of the load value W1 outputted from the first load detection means and the load value W2 outputted from the second load detection means when it is judged that the object has been on the bed platform from the judgment result of the bed occupancy state judgment step;

a head side load value storage step for storing the head side load value C calculated at the head side load value calculation step;

a head side load value decreased amount calculation step for calculating a decreased amount $\Delta$ of the head side load value C calculated at the head side load value calculation step within a predetermined time period;

a twelfth judgment step for judging whether or not a twelfth judgment formula (12) is satisfied, wherein the twelfth judgment formula (12) is given by $\Delta \geqq A \times s$, where $0 < s$ (s: previously set value); and a fourth notification step for notifying information that the object has raised his/her upper body when it is judged that the twelfth judgment formula is satisfied from the judgment result of the twelfth judgment step.

[9] The bed occupancy state detection method as recited in Item 8, further comprising a fourth communicating step for transmitting information that the object has raised his/her upper body when it is judged that the twelfth judgment formula is satisfied from the judgment result of the twelfth judgment step.

[10] The bed occupancy state detection method as recited in any one of Items 1 to 3, further comprising:

a total load value calculation step for calculating a total load value A which is a sum of four load values outputted from the first to fourth load detection means;

a total load value storage step for storing the total load value A calculated at the total load value calculation step;

a bed occupancy state judgment step for judging whether or not the object has been on the bed platform depending on whether or not the total load value A calculated at the total load value calculation step has maintained a predetermined load value or more for a predetermined time period;

an occupancy load value storage step of storing the total load value at the time when the predetermined time period has passed as an occupancy load value B in a state in which the object is on the bed platform when it is judged that the object has been on the bed platform from the judgment result of the bed occupancy state judgment step;

a ninth judgment step for judging whether or not a ninth judgment formula (9) is satisfied, wherein the ninth judgment formula (9) is given by $A \leq B \times m1$, where $0 < m1 < 1$ (m1: previously set value); and when it is judged that the ninth judgment formula is satisfied from a judgment result of the ninth judgment step, further comprising, a tenth judgment step for judging whether or not a tenth judgment formula (10) is satisfied, wherein the tenth judgment formula (10) is given by $A < B \times m2$, where $0 < m2 < m1$ (m2: previously set value); and a second notification step for notifying information that the object has got out of the bed when it is judged that the tenth judgment formula is satisfied from the judgment result of the tenth judgment step.

a maximum and minimum load value calculation step for calculating a maximum total load value Amax and a minimum total load value Amin of the total load value A calculated at the total load value calculation step within a predetermined time period;

an eleventh judgment step for judging whether or not an eleventh judgment formula (11) is satisfied, wherein the eleventh judgment formula (11) is given by $Amax - Amin \geq B \times q$, where $0 < q$ (q: previously set value); and a third notification step for notifying information on body movements of the object when it is judged that the eleventh judgment formula is satisfied from the judgment result of the eleventh judgment step;

a head side load value calculation step for calculating a head side load value C which is a sum of the load value W1 outputted from the first load detection means and the load value W2 outputted from the second load detection means when it is judged that the object has been on the bed platform from the judgment result of the bed occupancy state judgment step;

a head side load value storage step for storing the head side load value C calculated at the head side load value calculation step;

a head side load value decreased amount calculation step for calculating a decreased amount $\Delta$ of the head side load value C calculated at the head side load value calculation step within a predetermined time period;

a twelfth judgment step for judging whether or not a twelfth judgment formula (12) is satisfied, wherein the twelfth judgment formula (12) is given by $\Delta \geq A \times s$, where $0 < s$ (s: previously set value); and a fourth notification step for notifying information that the object has raised his/her upper body when it is judged that the twelfth judgment formula is satisfied from the judgment result of the twelfth judgment step.

[11] The bed occupancy state detection method as recited in Item 10, further comprising:

a first communication step for transmitting information on the bed occupancy state of the object when it is judged that at least one judgment formula is satisfied from the judgment result of the at least one judgment step among the first to eight judgment steps;

a second communicating step for transmitting information that the object has got out of the bed when it is judged that the tenth judgment formula is satisfied from the judgment result of the tenth judgment step;

a third communicating step for transmitting information on body movements of the object when it is judged that the eleventh judgment formula is satisfied from the judgment result of the eleventh judgment step; and a fourth communicating step for transmitting information that the object has raised his/her upper body when it is judged that the twelfth judgment formula is satisfied from the judgment result of the twelfth judgment step.

[12] A bed occupancy state detection apparatus, comprising:

first to fourth load detection means for detecting loads applied to a head side right portion, a head side left portion, a foot side right portion, and a foot side left portion of a bed platform, respectively;

wherein load values outputted form the first to fourth load detection means are defined as W1, W2, W3, and W4, respectively, first judgment means for judging whether or not a first judgment formula (1) is satisfied, wherein the first judgment formula (1) is given by $W1/(W1+W3) \leq n1$, where $0 < n1 < 0.5$ (n1: previously set value);

second judgment means for judging whether or not a second judgment formula (2) is satisfied, wherein the second judgment formula (2) is given by $W1/(W1+W3) \geq n2$, where $0.5 < n2 < 1$ (n2: previously set value);

third judgment means for judging whether or not a third judgment formula (3) is satisfied, wherein the third judgment formula (3) is given by $W2/(W2+W4) = < n3$, where $0 < n3 < 0.5$ (n3: previously set value);

fourth judgment means for judging whether or not a fourth judgment formula (4) is satisfied, wherein the fourth judgment formula (4) is given by $W2/(W2+W4) \geq n4$, where $0.5 < n4 < 1$ (n4: previously set value);

fifth judgment means for judging whether or not a fifth judgment formula (5) is satisfied, wherein the fifth judgment formula (5) is given by $W1/(W1+W2) \leq n5$, where $0 < n5 < 0.5$ (n5: previously set value);

sixth judgment means for judging whether or not a sixth judgment formula (6) is satisfied, wherein the sixth judgment formula (6) is given by $W1/(W1+W2) \geq n6$, where $0.5 < n6 < 1$ (n6: previously set value);

seventh judgment means for judging whether or not a seventh judgment formula (7) is satisfied, wherein the seventh judgment formula (7) is given by $W3/(W3+W4) \leq n7$, where $0 < n7 < 0.5$ (n7: previously set value);

eighth judgment means for judging whether or not an eighth judgment formula (8) is satisfied, wherein the eighth judgment formula (8) is given by $W3/(W3+W4) \geq n8$, where $0.5 < n8 < 1$ (n8: previously set value); and first notification means for notifying information on a bed occupancy state of an object in cases where it is judged that at least one judgment formula is satisfied from a judgment result of at least one judgment means among the first to eighth judgment means.

[13] The bed occupancy state detection apparatus as recited in Item 12, further comprising first communication means for transmitting information on the bed occupancy state of the object when it is judged that the judgment formula is satisfied in the judgment result of the at least one judgment means.

[14] The bed occupancy state detection apparatus as recited in Item 12 or 13, wherein the information on the bed occupancy state of the object is information that an occupancy position of the object is in an end region of the bed platform.

[15] The bed occupancy state detection apparatus as recited in any one of Items 12 to 14, further comprising:

total load value calculation means for calculating a total load value A which is a sum of four load values outputted from the first to fourth load detection means;

total load value storage means for storing the total load value A calculated by the total load value calculation means;

bed occupancy state judgment means for judging whether or not the object has been on the bed platform depending on whether or not the total load value A calculated at the total load value calculation means has maintained a predetermined load value or more for a predetermined time period;

occupancy load value storage means of storing the total load value at the time when the predetermined time has passed as a occupancy load value B in a state in which the object is on the bed platform when it is judged that the object has been on the bed platform from the judgment result of the bed occupancy state judgment means;

ninth judgment means for judging whether or not a ninth judgment formula (9) is satisfied, wherein the ninth judgment formula (9) is given by $A \leq B \times m1$, where $0 < m1 < 1$ (m1: previously set value); and when it is judged that the ninth judgment formula is satisfied from a judgment result of the ninth judgment means, further comprising, tenth judgment means for judging whether or not a tenth judgment formula (10) is satisfied, wherein the tenth judgment formula (10) is given by $A < B \times m2$, where $0 < m2 < m1$ (m2: previously set value); and second notification means for notifying information that the object has got out of the bed when it is judged that the tenth judgment formula is satisfied from the judgment result of the tenth judgment means.

[16] The bed occupancy state detection apparatus as recited in Item 15, further comprising second communication means for transmitting information that the object has got out of the bed when it is judged that the tenth judgment formula is satisfied from the judgment result of the tenth judgment means.

[17] The bed occupancy state detection apparatus as recited in any one of Items 12 to 14, further comprising:

total load value calculation means for calculating a total load value A which is a sum of four load values outputted from the first to fourth load detection means;

total load value storage means for storing the total load value A calculated at the total load value calculation means;

bed occupancy state judgment means for judging whether or not the object has been on the bed platform depending on whether or not the total load value A calculated at the total load value calculation means has maintained a predetermined load value or more for a predetermined time period;

occupancy load value storage means of storing the total load value at the time when the predetermined time period has passed as an occupancy load value B in a state in which the object is on the bed platform when it is judged that the object has been on the bed platform from the judgment result of the bed occupancy state judgment means;

maximum and minimum load value calculation means for calculating a maximum total load value Amax and a minimum total load value Amin of the total load value A calculated at the total load value calculation means within a predetermined time period;

eleventh judgment means for judging whether or not an eleventh judgment formula (11) is satisfied, wherein the eleventh judgment formula (11) is given by Amax−Amin $B \times q$, where $0 < q$ (q: previously set value); and third notification means for notifying information on body movements of the object when it is judged that the eleventh judgment formula is satisfied from the judgment result of the eleventh judgment means.

[18] The bed occupancy state detection apparatus as recited in Item 17, further comprising third communication means for transmitting information on body movements of the object when it is judged that the eleventh judgment formula is satisfied from the judgment result of the eleventh judgment means.

[19] The bed occupancy state detection apparatus as recited in any one of Items 12 to 14, further comprising:

total load value calculation means for calculating a total load value A which is a sum of four load values outputted from the first to fourth load detection means;

total load value storage means for storing the total load value A calculated at the total load value calculation means;

bed occupancy state judgment means for judging whether or not the object has been on the bed platform depending on whether or not the total load value A calculated at the total load value calculation means has maintained a predetermined load value or more for a predetermined time period;

head side load value calculation means for calculating a head side load value C which is a sum of the load value W1 outputted from the first load detection means and the load value W2 outputted from the second load detection means when it is judged that the object has been on the bed platform from the judgment result of the bed occupancy state judgment means;

head side load value storage means for storing the head side load value C calculated at the head side load value calculation means;

head side load value decreased amount calculation means for calculating a decreased amount Δ of the head side load value C calculated at the head side load value calculation means within a predetermined time period;

twelfth judgment means for judging whether or not a twelfth judgment formula (12) is satisfied, wherein the twelfth judgment formula (12) is given by $\Delta \geq A \times s$, where $0 < s$ (s: previously set value); and fourth notification means for notifying information that the object has raised his/her upper body when it is judged that the twelfth judgment formula is satisfied from the judgment result of the twelfth judgment means.

[20] The bed occupancy state detection apparatus as recited in Item 19, further comprising fourth communication means for transmitting information that the object has raised his/her upper body when it is judged that the twelfth judgment formula is satisfied from the judgment result of the twelfth judgment means.

[21] The bed occupancy state detection apparatus as recited in any one of Items 12 to 14, further comprising:

total load value calculation means for calculating a total load value A which is a sum of four load values outputted from the first to fourth load detection means;

total load value storage means for storing the total load value A calculated at the total load value calculation means;

bed occupancy state judgment means for judging whether or not the object has been on the bed platform depending on whether or not the total load value A calculated at the total load value calculation means has maintained a predetermined load value or more for a predetermined time period;

occupancy load value storage means of storing the total load value at the time when the predetermined time period has passed as an occupancy load value B in a state in which the object is on the bed platform when it is judged that the object has been on the bed platform from the judgment result of the bed occupancy state judgment means;

ninth judgment means for judging whether or not a ninth judgment formula (9) is satisfied, wherein the ninth judgment formula (9) is given by $A \geq B \times m1$, where $0 < m1 < 1$ (m1: previously set value); and when it is judged that the ninth judgment formula is satisfied from a judgment result of the ninth judgment means, further comprising, tenth judgment means for judging whether or not a tenth judgment formula (10) is satisfied, wherein the tenth judgment formula (10) is given by $A < B \times m2$, where $0 < m2 < m1$ (m2: previously set value); and second notification means for notifying information that the object has got out of the bed when it is judged that the tenth judgment formula is satisfied from the judgment result of the tenth judgment means, maximum and minimum load value calculation means for calculating a maximum total load value Amax and a minimum total load value Amin of the total load value A calculated at the total load value calculation means within a predetermined time period;

eleventh judgment means for judging whether or not an eleventh judgment formula (11) is satisfied, wherein the eleventh judgment formula (11) is given by $Amax - Amin \geq B \times q$, where $0 < q$ (q: previously set value); and third notification means for notifying information on body movements of the object when it is judged that the eleventh judgment formula (11) is satisfied from the judgment result of the eleventh judgment means;

head side load value calculation means for calculating a head side load value C which is a sum of the load value W1 outputted from the first load detection means and the load value W2 outputted from the second load detection means when it is judged that the object has been on the bed platform from the judgment result of the bed occupancy state judgment means;

head side load value storage means for storing the head side load value C calculated at the head side load value calculation means; head side load value decreased amount calculation means for calculating a decreased amount $\Delta$ of the head side load value C calculated at the head side load value calculation means within a predetermined time period;

twelfth judgment means for judging whether or not a twelfth judgment formula (12) is satisfied, wherein the twelfth judgment formula (12) is given by $\Delta \geq A \times s$, where $0 < s$ (s: previously set value); and fourth notification means for notifying information that the object has raised his/her upper body when it is judged that the twelfth judgment formula is satisfied from the judgment result of the twelfth judgment means.

[22] The bed occupancy state detection apparatus as recited in Item 21, further comprising:

first communication means for transmitting information on the bed occupancy state of the object when it is judged that at least one judgment formula is satisfied from the judgment result of the at least one judgment means among the first to eight judgment means;

second communication means for transmitting information that the object has got out of the bed when it is judged that the tenth judgment formula is satisfied from the judgment result of the tenth judgment means;

third communication means for transmitting information on body movements of the object when it is judged that the eleventh judgment formula is satisfied from the judgment result of the eleventh judgment means; and fourth communication means for transmitting information that the object has raised his/her upper body when it is judged that the twelfth judgment formula is satisfied from the judgment result of the twelfth judgment means.

[23] A bed occupancy state monitoring system, comprising:

first to fourth load detection means for detecting loads applied to a head side right portion, a head side left portion, a foot side right portion, and a foot side left portion of a bed platform, respectively;

wherein load values outputted form the first to fourth load detection means are defined as W1, W2, W3, and W4, respectively, first judgment means for judging whether or not a first judgment formula (1) is satisfied, wherein the first judgment formula (1) is given by $W1/(W1+W3) \leq n1$, where $0 < n1 < 0.5$ (n1: previously set value);

second judgment means for judging whether or not a second judgment formula (2) is satisfied, wherein the second judgment formula (2) is given by $W1/(W1+W3) \geq n2$, where $0.5 < n2 < 1$ (n2: previously set value);

third judgment means for judging whether or not a third judgment formula (3) is satisfied, wherein the third judgment formula (3) is given by $W2/(W2+W4) \leq n3$, where $0 < n3 < 0.5$ (n3: previously set value);

fourth judgment means for judging whether or not a fourth judgment formula (4) is satisfied, wherein the fourth judgment formula (4) is given by $W2/(W2+W4) \geq n4$, where $0.5 < n4 < 1$ (n4: previously set value);

fifth judgment means for judging whether or not a fifth judgment formula (5) is satisfied, wherein the fifth judgment formula (5) is given by $W1/(W1+W2) \leq n5$, where $0 < n5 < 0.5$ (n5: previously set value);

sixth judgment means for judging whether or not a sixth judgment formula (6) is satisfied, wherein the sixth judgment formula (6) is given by $W1/(W1+W2) \geq n6$, where $0.5 < n6 < 1$ (n6: previously set value);

seventh judgment means for judging whether or not a seventh judgment formula (7) is satisfied, wherein the seventh judgment formula (7) is given by $W3/(W3+W4) \leq n7$, where $0 < n7 < 0.5$ (n7: previously set value);

eighth judgment means for judging whether or not an eighth judgment formula (8) is satisfied, wherein the eighth judgment formula (8) is given by $W3/(W3+W4) \geq n8$, where $0.5 < n8 < 1$ (n8: previously set value); and notification means for notifying information on a bed occupancy state of an object in cases where it is judged that at least one judgment formula is satisfied from a judgment result of at least one judgment means among the first to eighth judgment means.

EFFECTS OF THE INVENTION

The present invention has the following effects.

In the invention [1], since the invention includes the first to eighth judgment steps, values corresponding to various lying postures of an object can be detected.

Furthermore, the judgment formula of each judgment step does not include a length size and a width size of a bed platform. This enables the judgment without using the length size and/or the width size of the bed platform, i.e., without using the size of the bed platform. Therefore, for example, in detecting the bed occupancy state of the object, it is not required to previously set sizes such as the length or the width of the bed platform. Accordingly, it is possible to easily perform the detection of the bed occupancy state of the object on a bed having various size.

Furthermore, the invention includes the first notification step, and therefore the information on the bed occupancy state of the object can be notified to a nurse, a care personnel, or a monitoring personnel, as a notification recipient.

In the invention [2], the information on the occupancy state of the object can be transmitted.

In the invention [3], the information that the occupancy position of the object is in the end region of the bed platform can be notified or transmitted.

In the invention [4], the invention includes the ninth judgment step and the tenth judgment step, and therefore it is possible to judge whether or not the object has got out of the bed as the information on the bed occupancy state of the object.

Further, the invention includes the second notification step, and therefore the information that the object has got out of the bed can be notified to a nurse, a care personnel, a monitoring personnel, etc.

In the invention [5], it is possible to transmit the information that the object has got out of the bed can be transmitted.

In the invention [6], the invention includes the eleventh judgment step, and therefore it is possible to judge whether or not there are body movements of the object as the information on the bed occupancy state of the object.

Furthermore, this detection method includes the third notification step, and therefore it is possible to notify a nurse, a care personnel, a monitoring personnel, etc. of the information on the bed occupancy state of the object.

In the invention [7], the information on body movements of the object can be transmitted.

In the invention [8], the invention includes the twelfth judgment step, and therefore it is possible to judge whether or not the object has raised his/her upper body as information on the bed occupancy state of the object.

Furthermore, the invention includes the fourth notification step, and therefore the information that the object has raised his/her upper body can be notified to a nurse, a care personnel, a monitoring personnel, etc.

In the invention [9], the information that the object has raised his/her upper body can be transmitted.

In the invention [10], the effects of the invention [1], [4], [6] and [8] can be exerted.

In the invention [11], the effects of the invention [2], [5], [7] and [9] can be exerted.

In the invention [12] to [22], a bed occupancy state detection apparatus preferably used for the bed occupancy state detection method according to the invention [1] to [11] can be provided.

In the invention [23], the bed occupancy state of the object can be monitored assuredly.

DESCRIPTION OF THE REFERENCE NUMERALS

Figure 1:
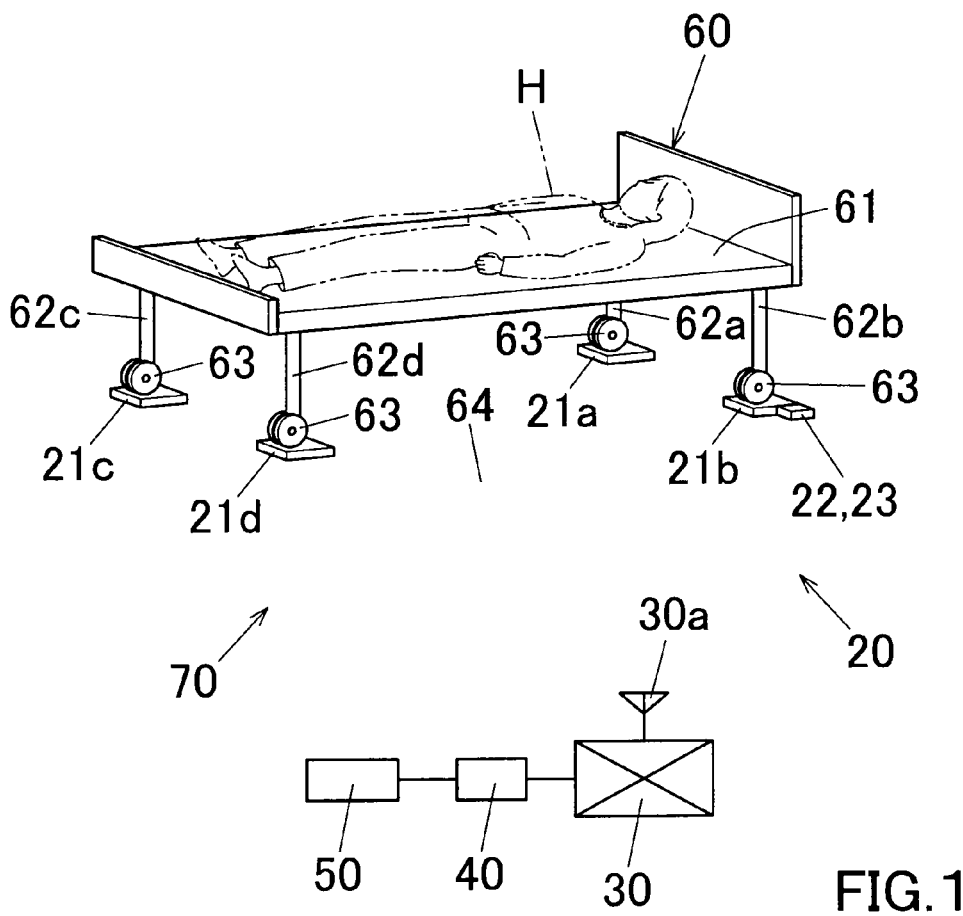
FIG. 1 is a schematic view showing a bed occupancy state detection apparatus according to an embodiment of the invention.

20 . . . bed occupancy state detection apparatus
21$a$ . . . first load detection means
21$b$ . . . second load detection means
21$c$ . . . third load detection means
21$a$ . . . fourth load detection means
22 . . . control device
30 . . . calculation device
31 . . . calculation portion
31$a$ . . . load value calculation means
31$c$ . . . total load value calculation means
31$d$ . . . maximum and minimum load value calculation means
31$e$ . . . head side load value calculation means
31$f$ . . . head side load value decreased amount calculation means
32 . . . storage portion
32$a$ . . . total load value storage means
32$b$ . . . occupancy load value storage means
32$c$ . . . head side load value storage means
32$d$ . . . set value storage means
33 . . . judgment portion
33$a$ . . . first judgment means
33$b$ . . . second judgment means
33$c$ . . . third judgment means
33$d$ . . . fourth judgment means
33$e$ . . . fifth judgment means
33$f$ . . . sixth judgment means
33$g$ . . . seventh judgment means
33$h$ . . . eighth judgment means
33$i$ . . . ninth judgment means
33$j$ . . . tenth judgment means
33$k$ . . . eleventh judgment means
33$l$ . . . twelfth judgment means
33$m$ . . . occupancy judgment means
40 . . . second communication device
40$a$ . . . first communication means
40$b$ . . . second communication means
40$c$ . . . third communication means
40$d$ . . . fourth communication means
50 . . . notification device
50$a$ . . . first notification means
50$b$ . . . second notification means
50$c$ . . . third notification means
50$d$ . . . fourth notification means
60 . . . bed
61 . . . bed platform
70 . . . bed occupancy state monitoring system
H . . . object

BEST MODE FOR CARRYING OUT THE INVENTION

Next, an embodiment of the present invention will be explained with reference to the drawings.

In FIG. 1, the reference numeral "20" denotes a bed occupancy state detection apparatus according to an embodiment of the present invention, and "60" denotes a bed.

Figure 2:
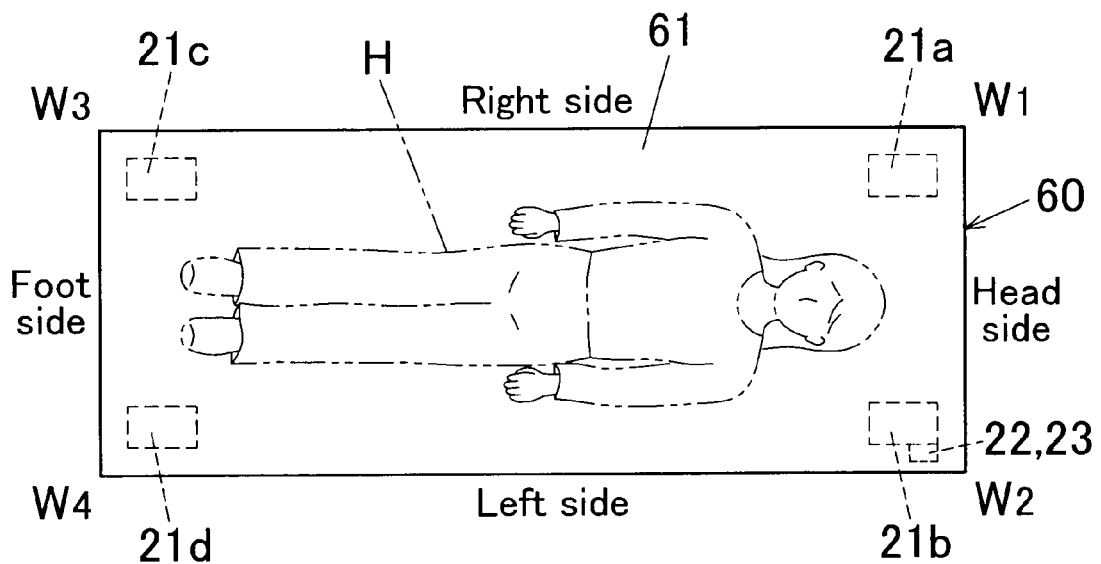
FIG. 2 is a schematic plan view showing a bed platform.

The bed 60 is furniture for use in medical facilities (e.g., hospitals), aged person facilities, nursing-care facilities, nursing homes, hotels, ordinary homes, etc. As shown in FIG. 2, the platform 61 of the bed 60 is formed into a rectangular shape as seen from the top. This bed 60 is, as shown in FIG. 1, placed on a bed placing surface 64 which is a floor in a patient's room, an examination room, a lodging room, a bed room, etc.

For the explanatory purpose, in this specification, as shown in FIGS. 1 and 2, in the state in which an object H lies down on the platform 61 of the bed 20 in a face-up posture, the head side of the object H is defined as "head side of the platform 61," the leg side of the object is defined as "foot side of the platform 61," "the right side of the object is defined as "right side of the platform 61," and the left side of the object is defined as "left side of the platform 61."

As shown in FIG. 1, the bed 20 has a total of four leg portions, i.e., a head side right leg portion 62a, a head side left leg portion 62b, a foot side right leg portion 62c, and a foot side left leg portion 62d, for supporting the platform 21 generally horizontally at a certain height position. At the lower end of each of the leg portions 62a, 62b, 62c, and 62d, a rotatable bed moving caster 63 is provided. In this invention, however, it is not always required to provide a caster 63 at the lower end of each of the leg portions 62a, 62b, 62c and 62d.

On this bed platform 62, as an object H, a sick person, a dementia patient, an aged person, a healthy person, an infant, a hotel guest, etc., lies down in various lying down postures (e.g., in a face-up posture, in a lateral position, or in a face-down posture) for, e.g., sleep, rest, medical treatment, medical examination or inspection, etc.

In the present invention, the bed 60 is not limited to a bed for sleep or rest, and can be, for example, an examination table, an inspection bench, a stretcher, a sofa, etc.

The bed occupancy state detection apparatus 20 according to this embodiment is used to detect the bed occupancy state of an object on a bed platform, such as, e.g., values corresponding to the lying postures, getting out of a bed, getting onto a bed, presence or absence of body movements, or whether or not an object H has raised his/her upper body.

Figure 3:
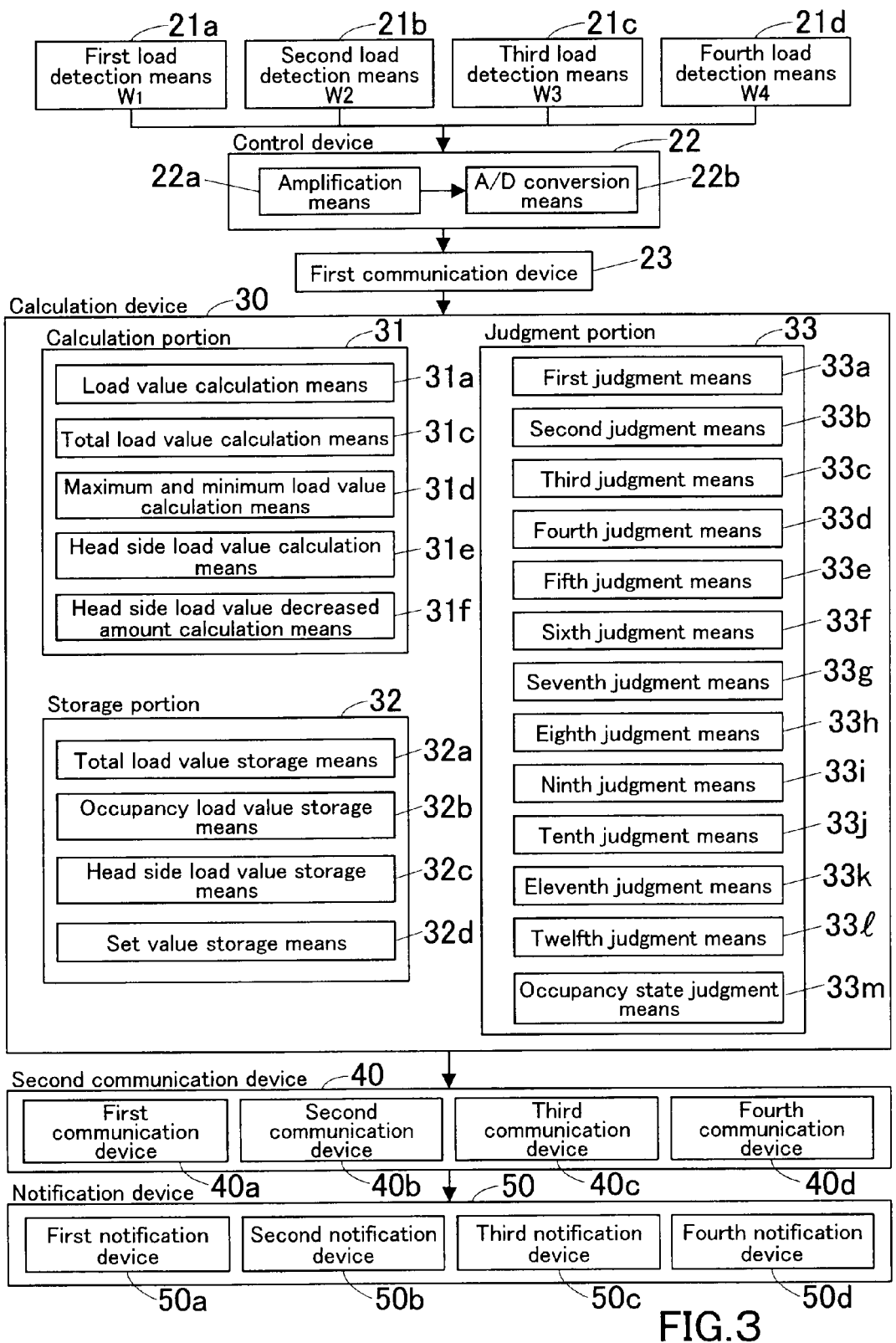
FIG. 3 is a block diagram showing the structure of the detection apparatus.

As shown in FIGS. 1 and 3, this detection apparatus 20 is provided with the first to fourth load detection means 21a, 21b, 21c, and 21d, a control device 22, a first communication device 23, an calculation device 30, a second communication device 40, and a notification device 50.

The first load detection means 21a detects the load applied to the head side right portion (in detail, the head side right end portion) of the bed platform 61 in a temporally continuous manner (i.e., every predetermined times). This first load detection means 21a is disposed between the caster 63 of the head side right leg portion 62a of the bed 60 and the bed placing surface 64.

The second load detection means 21b detects the load applied to the head side left portion (in detail, the head side left end portion) of the bed platform 61 in a temporally continuous manner. This second load detection means 21b is disposed between the caster 63 of the head side left leg portion 62b of the bed 60 and the bed placing surface 64.

The third load detection means 21c detects the load applied to the foot side right portion (in detail, the foot side right end portion) of the bed platform 61 in a temporally continuous manner. This third load detection means 21c is disposed between the caster 63 of the foot side right leg portion 62c of the bed 60 and the bed placing surface 64.

The fourth load detection means 21d detects the load applied to the foot side left portion (in detail, the foot side left end portion) of the bed platform 61 in a temporally continuous manner. This fourth load detection means 21d is disposed between the caster 63 of the foot side left leg portion 62d of the bed 60 and the bed placing surface 64.

Each of the load detection means 21a, 21b, 21c and 21d is a commercially available load detector, such as, e.g., a load cell having a strain gauge.

The number of times of load detections per one second by each load detection means 21a, 21b, 21c, and 21d is preferably set to 2 times or more/sec. It is more preferable that the number of times is set to 4 times or more/sec. but not more than 100 times/sec. In the present invention, however, it is not required that the number of times of load detections per one second by each of the load detection means 21a, 21b, 21c, and 21d falls within the aforementioned range.

In this embodiment, each of the load detection means 21a, 21c, 21c, 21d outputs a voltage corresponding to the load applied to each portion of the bed platform 61 as a load value.

As shown in FIG. 3, the control device 22 has an amplification means 22a and an analog-digital conversion means (A/D conversion means) 22b. This control device 22 is attached to, for example, one of the load detection means 21b among the first to fourth load detection means 21a, 21b, 22c, and 22d.

The amplification means 22a is configured to amplify the voltage representing the load value outputted from each of the load detection means 21a, 21b, 21c, and 21d. The analog-digital conversion means 22b is configured to convert the voltage amplified by the amplification means 22a from an analog signal into a digital signal.

The first communication device 23 is configured to transmit the voltage (digital signal) converted by the analog-digital conversion means 22b to the calculation device 30 via a wired or wireless communication network, such as, e.g., a telephone line network, the Internet, a wired LAN, or a wireless LAN. In this embodiment, the first communication device 23 is configured to transmit the signal to the calculation device 30 via a wireless communication network. In FIG. 1, "30a" denotes a receiver antenna portion of the calculation device 30 for receiving the signal transmitted from the first communication device 23.

The calculation device 30 is equipped with a calculation portion 31, a storage portion 32, and a judgment portion 33. This calculation device 30 is constituted by a computer having ROMs, RAMS, other memories, CPUs, etc. This calculation device 30 is placed in a room where the bed 60 is installed, or placed in a monitoring room, a nurse station, a waiting room for patients, etc., or mounted in a mobile telephone device (including a PHS device).

The calculation portion 31 includes a load value calculation means 31, a total load value calculation means 31c, a maximum and minimum load value calculation means 31d, a head side load value calculation means 31e, and a head side load value decreased amount calculation means 31f.

The storage portion 32 includes a total load value storage means 32a, an occupancy load value storage means 32b, a head side load value storage means 32c, and a set value storage means 32d. Furthermore, the storage portion 32 has, for example, a storage means (not illustrated) for storing programs and prescribed judgment formulas required to detect the bed occupancy state of the object H.

The judgment portion 33 has first to twelfth judgment means 33a, 33b, 33c, 33d, 33e, 33f, 33g, 33h, 33i, 33j, 33k, and 33l, and a bed occupancy state judgment means 33m.

The load value calculation means 31a is configured to calculate the load applied to each portion of the bed platform 61, which represents the load value outputted from each of the load detection means 21a, 21b, 21c, and 21d, in a temporally continuous manner based on the voltage (digital signal) outputted from each of the load detection means 21a, 21b, 21c, and 21d. This load value calculation means 31a is configured so that it also can perform a tare process which subtracts the load of the bed 61 in a state in which an object H is not occupying the bed platform 61, i.e., only the load of the bed 61.

Here, the load values outputted from the first to fourth load detection means 21a, 21b, 21c, and 21d are defined as W1 to W4, respectively, and the voltages outputted from the first to fourth load detection means 21a, 21b, 21c, and 21d are defined as V1 to V4, respectively. Then, W1, W2, W3, and W4 can be calculated from the following formulas (i) to (iv).

$$W1 = a1 \times V1 + b1 \qquad \text{Formula (i)}$$

$$W2 = a2 \times V2 + b2 \qquad \text{Formula (ii)}$$

$$W3 = a3 \times V3 + b3 \qquad \text{Formula (iii)}$$

$$W4 = a4 \times V4 + b4 \qquad \text{Formula (iv)}$$

where W1 to W4 and V1 to V4 are defined as follows:

W1: load value outputted from the first load detection means 21a

W2: load value outputted from the second load detection means 21b

W3: load value outputted from the third load detection means 21c

W4: load value outputted from the fourth load detection means 21d

V1: voltage outputted from the first load detection means 21a

V2: voltage outputted from the second load detection means 21b

V3: voltage outputted from the third load detection means 21c

V4: voltage outputted from the fourth load detection means 21d

Furthermore, a1, a2, a3, and a4 are previously set constant numbers, and a1≠0, a2≠0, a3≠0, and a4≠0. b1, b2, b3, and b4 are previously set constant numbers.

W1 to W4 are values in which only the load of the bed 51 is subtracted, i.e., the value after the tare process. In the present invention, W1 to W4 can be values before the tare process, i.e., values including the load of the bed 60 as the tare.

W1 corresponds to the load after the tare process applied to the head side right portion of the bed platform 61. W2 corresponds to the load after the tare process applied to the head side left portion of the bed platform 61. W3 corresponds to the load after the tare process applied to the foot side right portion of the bed platform 61. W4 corresponds to the load after the tare process applied to the foot side left portion of the bed platform 61.

In the present invention, however, as the load values outputted form the first to fourth load detection means 21a, 21b, 21c, and 21d, other than the above, for example, the voltages V1, V2, V3, and V4 after the tare process or before the tare process outputted from the first to fourth load detection means 21a, 21b, 21c, and 21d can be used. In this case, between V1 to V4 and W1 to W4, there are relations of the aforementioned Formulas (i) to (iv), respectively.

The number of calculations per second by the load value calculation means 31a is set, for example, to be the same as the number of load detections per second by each of the first to fourth load detection means 21a, 21b, 21c, and 21d.

The total load value calculation means 31c is configured to calculate the total load value A which is a sum of four load values outputted from the first to fourth load detection means 21a, 21b, 21c, and 21d in a temporally continuous manner. That is, the total load value A can be calculated by the following formula (v).

$$A = W1 + W2 + W3 + W4 \qquad \text{Formula (v)}$$

The number of calculations per second by the total load value calculation means 31c is set, for example, to be the same as the number of load detections per second by each of the first to fourth load detection means 21a, 21b, 21c, and 21d.

The total load value storage means 32a is configured to store the total load value A calculated by the total load value calculation means 31c in a temporally continuous manner.

The number of storages per second by the total load value storage means 32a is set, for example, to be the same as the number of calculations per second by the total load value calculation means 31c.

The occupancy judgment means 33m is configured to judge whether or not an object H has been on the bed platform 61 depending on whether or not the total load value A calculated by the total load value calculation means 31c has maintained a predetermined load value or more for a predetermined time period. More specifically, this occupancy judgment means 33m judges that an object H has been on the bed platform 61 when the total load value A maintains the predetermined load value or more for the predetermined time period. Otherwise, it judges that the object H has not been on the bed platform 61.

In this occupancy judgment means 33m, the aforementioned predetermined time period can be, for example, within the range of 5 to 300 seconds. The aforementioned predetermined load value or more can be, for example, ½ or more, more preferably ¾ or more, of the body weight of the object H. It should be noted that the upper limit of the predetermined load value is not limited. The predetermined load value can be set to, for example, the body weight or less of the object H. In the present invention, however, the predetermined time period and the predetermined load value are not required to fall within the aforementioned ranges, and can be changed variously depending on, e.g., the body status, the body weight, or the body height of the object H, or the facility using the detection apparatus 20.

1 kgf is 9.80665N, and therefore 1 kgf is about 9.8N.

The occupancy load value storage means 32b is configured to store, when it is judged that the object H has been on the bed platform 61 from the judgment result by the occupancy judgment means 33m, the total load value A at the time when the aforementioned predetermined time period has passed by the occupancy judgment means 33m as the load value in a state in which the object H is on the bed platform 61, i.e., the occupancy load value B.

The head side load value calculation means 31e is configured to calculate, when it is judged that the object H has been on the bed platform 61 from the judgment result by the occupancy judgment means 33m, the load value which is a sum of the load value W1 outputted from the first load detection means 21a and the load value W2 outputted from the second load detection means 21b, as a head side load value C in a temporally continuous manner. That is, the head side load value C is calculated by the following formula (vi).

$$C = W1 + W2 \quad \text{Formula (vi)}$$

The number of calculations per second by the head side load value calculation means 31e is set, for example, to be the same as the number of calculations per second by the load value calculation means 31a.

The head side load value storage means 32c is configured to store the head side load value C calculated by the head side load value calculation means 31e in a temporally continuous manner.

The number of storages per second by the head side load storage means 32c is set, for example, to be the same as the number of calculations per second by the head side load value calculation means 31e.

The head side load value decreased amount calculation means 31f is configured to calculate the decreased amount Δ of the head side load value C calculated by the head side load value calculation means 31e in a predetermined time period. The predetermined time period can be, for example, within the range of 3 to 180 seconds. In the present invention, however, it should be noted that the predetermined time period is not limited to fall within the aforementioned range and can be variously changed depending on, for example, the body status, the body weight, the body length of the object H, or the facility in which the detection apparatus 20 is installed.

If the current head side load value C is defined as $C_{(t0)}$ and the head side load value of T seconds before the current time is defined as $C_{(t0-T)}$, Δ is calculated by the following formula (vii).

$$\Delta C = C_{(t0-T)} - C_{(t0)} \quad \text{Formula (vii)}$$

The number of calculations per second by the head side load value decreased amount calculation means 31f is set, for example, to be the same as the number of calculations per second by the head side load value calculation means 31e.

The maximum and minimum load value calculation means 31d is configured to calculate the maximum total load value "Amax" and the minimum total load value "Amin" of the total load value calculated by the total load value calculation means 31c within a predetermined time period in a temporally continuous manner. The predetermined time period can be, for example, within the range of 3 to 180 seconds. In the present invention, however, it should be noted that the predetermined time period is not limited to fall within the aforementioned range and can be variously changed depending on, for example, the body status, the body weight, the body length of the object H, or the facility in which the detection apparatus 20 is installed.

The number of calculations per second by the maximum and minimum load value calculation means 31d can be set, for example, to be the same as the number of calculations by the load value calculation means 31a per second.

The first judgment means 33a is configured to judge whether or not the following first judgment formula (1) is satisfied, based on the load value W1 outputted form the first load value detection means 21a and the load value W3 outputted form the third load value detection means 21c.

$$W1/(W1+W3) \leq n1 \quad \text{Formula (1)}$$

wherein "n1" is a previously set value (first threshold value) and 0<n1<0.5. Specifically, "n1" is, for example, 0<n1<0.25.

The second judgment means 33b is configured to judge whether or not the following second judgment formula (2) is satisfied, based on the load value W1 outputted form the first load value detection means 21a and the load value W3 outputted form the third load value detection means 21c.

$$W1/(W1+W3) \geq n2 \quad \text{Formula (2)}$$

wherein "n2" is a previously set value (second threshold value) and 0.5<n2<1. Specifically, "n2" is, for example, 0.75<n2<1.

The third judgment means 33c is configured to judge whether or not the following third judgment formula (3) is satisfied, based on the load value W2 outputted form the second load value detection means 21b and the load value W4 outputted form the fourth load value detection means 21d.

$$W2/(W2+W4) \leq n3 \quad \text{Formula (3)}$$

wherein "n3" is a previously set value (third threshold value) and 0<n3<0.5. Specifically, "n3" is, for example, 0<n3<0.25.

The fourth judgment means 33d is configured to judge whether or not the following fourth judgment formula (4) is satisfied, based on the load value W2 outputted form the second load value detection means 21b and the load value W4 outputted form the fourth load value detection means 21d.

$$W2/(W2+W4) \geq n4 \quad \text{Formula (4)}$$

wherein "n4" is a previously set value (fourth threshold value) and 0.5<n4<1. Specifically, "n4" is, for example, 0.75<n4<1.

The fifth judgment means 33e is configured to judge whether or not the following fifth judgment formula (5) is satisfied, based on the load value W1 outputted form the first load value detection means 21a and the load value W2 outputted form the second load value detection means 21b.

$$W1/(W1+W2) \leq n5 \quad \text{Formula (5)}$$

wherein "n5" is a previously set value (fifth threshold value) and 0<n5<0.5. Specifically, "n5" is, for example, 0<n5<0.25.

The sixth judgment means 33f is configured to judge whether or not the following sixth judgment formula (6) is satisfied, based on the load value W1 outputted form the first load value detection means 21a and the load value W2 outputted form the second load value detection means 21b.

$$W1/(W1+W2) \geq n6 \quad \text{Formula (6)}$$

wherein "n6" is a previously set value (sixth threshold value) and 0.5<n6<1. Specifically, "n6" is, for example, 0.75<n6<1.

The seventh judgment means 33g is configured to judge whether or not the following seventh judgment formula (7) is satisfied, based on the load value W3 outputted form the third load value detection means 21c and the load value W4 outputted form the fourth load value detection means 21d.

$$W3/(W3+W4) \leq n7 \quad \text{Formula (7)}$$

wherein "n7" is a previously set value (seventh threshold value) and 0<n7<0.5. Specifically, "n7" is, for example, 0<n7<0.25.

The eighth judgment means 33h is configured to judge whether or not the following eighth judgment formula (8) is satisfied, based on the load value W3 outputted form the third load value detection means 21c and the load value W4 outputted form the fourth load value detection means 21d.

$$W3/(W3+W4) \geq n8 \quad \text{Formula (8)}$$

wherein "n8" is a previously set value (seventh eighth value) and 0.5<n8<1. Specifically, "n8" is, for example, 0.75<n8<1.

In the present invention, the aforementioned n1, n2, n3, n4, n5, n6, n7, and n8 are not required to fall within the aforementioned ranges, and can be variously changed depending on, for example, the body status, the body weight, the body length of the object H, the size of the bed platform 61, or the facility in which the detection apparatus 20 is installed.

The ninth judgment means 33$i$ is configured to judge whether or not the following ninth judgment formula (9) is satisfied, based on the total load value A calculated by the total load value calculation means 31$c$ and the occupancy load value B stored in the occupancy load value storage means 32$b$.

$$A \leq B \times m1 \quad \text{Formula (9)}$$

wherein "m1" is a previously set value, and 0<m1<1. Specifically, "m1" is, for example, 0.5<m1<0.9.

The tenth judgment means 33$j$ is configured to judge whether or not the following tenth judgment formula (10) is satisfied, based on the total load value A calculated by the total load value calculation means 31$c$ and the occupancy load value B stored in the occupancy load value storage means 32$b$.

$$A < B \times m2 \quad \text{Formula (10)}$$

wherein "m2" is a previously set value and 0<m2<m1. Specifically, "m2" is, for example, 0<m2<0.5.

In the present invention, the aforementioned m1 and m2 are not required to fall within the aforementioned ranges, and can be variously changed depending on, for example, the body status, the body weight, the body length of the object H, the size of the bed platform 61, or the facility in which the detection apparatus 20 is installed.

The eleventh judgment means 33$k$ is configured to judge whether or not the following eleventh judgment formula (11) is satisfied, based on the maximum load value Amax and minimum load value Amin calculated by the maximum and minimum load value calculation means 31$d$ and the occupancy load value B stored in the occupancy load value storage means 32$b$.

$$A\text{max} - A\text{min} \geq B \times q \quad \text{Formula (11)}$$

wherein "q" is a previously set value, and 0<q Specifically, "q" is, for example, $0.05 \leq q \leq 0.2$.

In the present invention, the aforementioned "q" is not required to fall within the aforementioned range, and can be variously changed depending on, for example, the body status, the body weight, the body length of the object H, the size of the bed platform 61, or the facility in which the detection apparatus 20 is installed.

The twelfth judgment means 33$l$ is configured to judge whether or not the following twelfth judgment formula (12) is satisfied, based on the total load value A calculated by the total load value calculation means 31$c$ and the decreased amount Δ of the head side load value calculated by the head side load value decreased amount calculation means 31$f$.

$$\Delta C \geq A \times s \quad \text{Formula (12)}$$

wherein "s" is a previously set value, and 0<s. Specifically, "s" is, for example, $0.05 \leq s \leq 0.2$.

In the present invention, the aforementioned "s" is not required to fall within the aforementioned range, and can be variously changed depending on, for example, the body status, the body weight, the body length of the object H, the size of the bed platform 61, or the facility in which the detection apparatus 20 is installed.

The number of judgments by each judgment means 33$a$ to 33$l$ per second is set, for example, to be the same as the number of calculations by the load value calculation means 31$a$ per second.

The set value storage means 32$d$ is configured to preliminary set and store prescribed values, such as, e.g., n1 to n8, m1, m2, q, s, a1 to a4, or b1 to b4, etc. The calculation device 30 is equipped with an input means for inputting predetermined values to make the set value storage means 32$d$ store the predetermined values.

The notification device 50 is equipped with the first to fourth notification means 50$a$, 50$b$, 50$c$, and 50$d$. This notification device 50 can be placed, for example, in a monitoring room, a nurse station, a waiting room for patients, etc., or mounted in a mobile telephone device (including a PHS device).

The first notification means 50$a$ is configured to notify a nurse, a care personnel, a monitoring personnel, etc., as a notification recipient of the information on the bed occupancy state of the object H when it is judged that the judgment formula is satisfied from the judgment result of at least one of the first to eight judgment means 33$a$, 33$b$, 33$c$, 33$d$, 33$e$, 33$f$, 33$g$, and 33$h$. In this embodiment, the first notification means 50$a$ is configured to provide the information that the occupied position of the object H is in the end region of the bed platform 61 as the information on the bed occupancy state of the object H.

The end region of the bed platform 61 includes, for example, the right end region, the left end region, the head side end region, and the foot side end region of the bed platform 61. The right end region of the bed platform 61 can be set, for example, to the width region of 100 to 250 mm from the right side edge of the bed platform 61, and the left end region of the bed platform 61 can be set, for example, to the width region of 100 to 250 mm from the left side edge of the bed platform 61. Further, the head side end region of the bed platform 61 can be set, for example, to the width region of 100 to 500 mm from the head side end edge of the bed platform 61, and the foot side end region of the bed platform 61 can be set, for example, to the width region of 100 to 500 mm from the foot side end edge of the bed platform 61. In the present invention, however, the end regions of the bed platform 61 are not limited to the aforementioned regions, and can be variously changed depending on, for example, the body status, the body weight, the body length of the object H, the size of the bed platform 61, or the facility in which the detection apparatus 20 is installed.

The second notification means 50$b$ is configured to notify a nurse, a care personnel, a monitoring personnel, etc., as a notification recipient of information that the object H has got off the bed, when it is judged that the tenth judgment formula 10 is satisfied from the judgment result of the tenth judgment means 33$j$.

The third notification means 50$c$ is configured to notify a nurse, a care personnel, a monitoring personnel, etc., as a notification recipient of the information on the body movements of the object H, when it is judged that the eleventh judgment formula 11 is satisfied from the judgment result of the eleventh judgment means 33$k$. In this embodiment, the third notification means 50$c$ is configured to provide the information that there are body movements of the object H as the information on the body movements of the object H.

The fourth notification means 50$d$ is configured to notify a nurse, a care personnel, a monitoring personnel, etc., as a notification recipient of the information that the object H has raised his/her upper body, when it is judged that the twelfth judgment formula 12 is satisfied from the judgment result of the twelfth judgment means 33l.

Each notification means 50a, 50b, 50c, and 50d has a notification speaker, a notification lamp, a display means, etc. The notification speaker notifies a notification recipient of the prescribed information using sound such as voice or buzzer sound. The notification lamp notifies a notification recipient of the prescribed information by turning-on or blinking a lamp. The notification display means includes a liquid crystal display, a CRT, etc., and notifies a notification recipient of the prescribed information by displaying characters, graphics, etc., thereon.

The second communication device 40 is equipped with the first to fourth communication means 40a, 40b, 40c, and 40d. This second communication device 40 is equipped, for example, in the calculation device 30.

The first communication means 40a is configured to transmit the information on the bed occupancy state of the object H to the first notification means 50a via a wireless communication network or a wired communication network, such as, e.g., a telephone line network, the internet, a wired LAN, or a wireless LAN, etc., when it is judged that the judgment formula is satisfied from the judgment by at least one of judgment means among the first to eight judgment means 33a, 33b, 33c, 33d, 33e, 33f, 33g, and 33h. In this embodiment, the first communication means 40a transmits the information that the occupancy position of the object H is in the end region of the bed platform 61 as the information on the bed occupancy state of the object H.

The second communication means 40b is configured to transmit the information that the object H has got out of the bed to the second notification means 50b via a wireless communication network or a wired communication network, when it is judged that the tenth judgment formula 10 is satisfied from the judgment result of the tenth judgment means 33j.

The third communication means 40c is configured to transmit the information on the body movements of the object H to the third notification means 50c via a wireless communication network or a wired communication network, when it is judged that the eleventh judgment formula 11 is satisfied from the judgment result of the eleventh judgment means 33k. In this embodiment, the third communication means 40c transmits the information that there are body movements of the object H as the information on the body movements of the object H.

The fourth communication means 40d is configured to transmit the information that the object H has raised his/her upper body to the fourth notification means 50d via a wireless communication network or a wired communication network, when it is judged that the twelfth judgment formula 12 is satisfied from the judgment result of the twelfth judgment means 33l.

In each communication means 40a, 40b, 40c, and 40d, as a telephone line network, a circuit network for a mobile telephone (including PHS) and a circuit network for a land-line telephone can be used.

Next, a method of detecting a bed occupancy state using the aforementioned detection apparatus 20 will be explained based on the flowchart shown in FIGS. 4 to 8.

Figure 4:
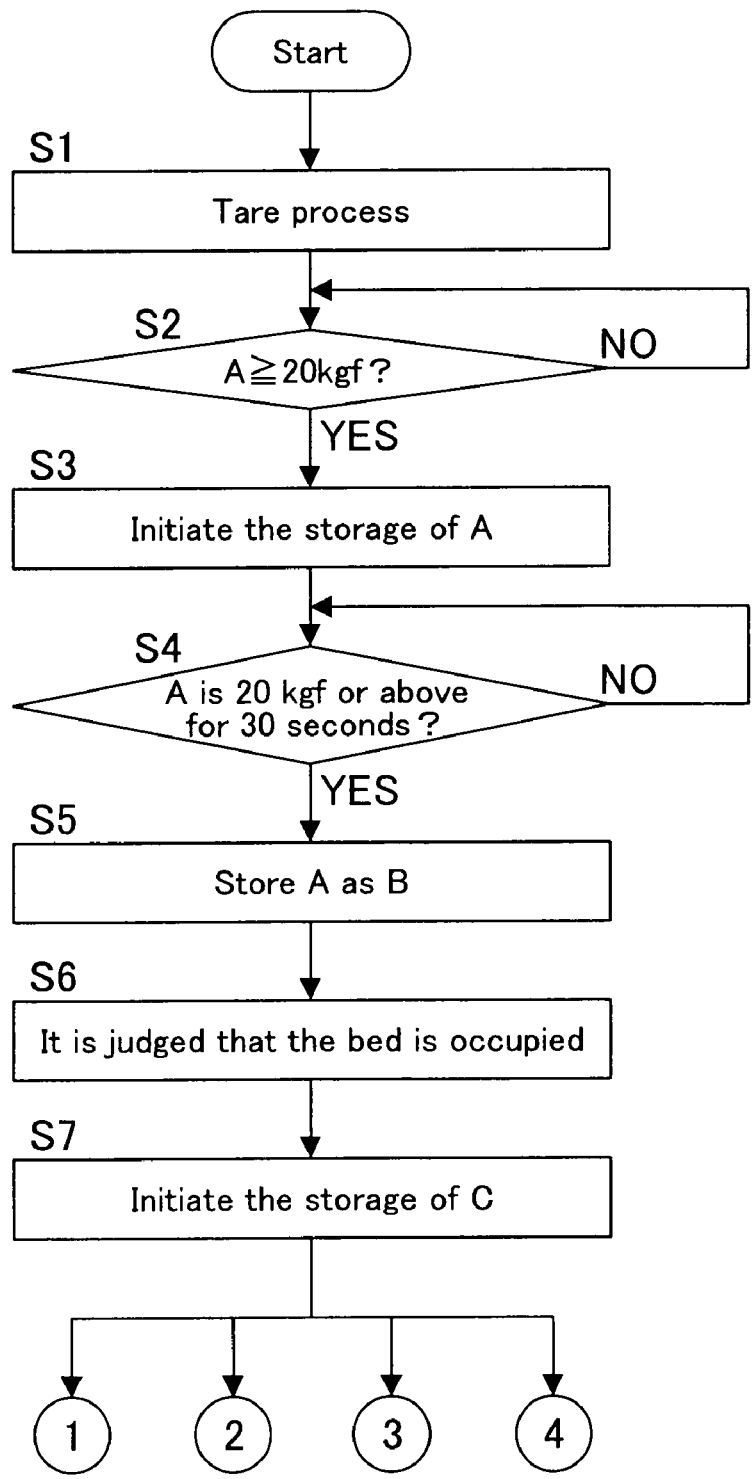
FIG. 4 is a flowchart of a bed occupancy state detection method using the detection apparatus.

As shown in FIG. 4, at Step S1, the loads applied to the head side right portion, the head side left portion, the foot side right portion, and the foot side left portion of the bed platform 61 are detected by the first to fourth load detection means 21a, 21b, 21c, and 21d, respectively [Load Detection Step]. At this time, the load value outputted form each of the first to fourth load detection means 21a, 21b, 21c, 21d is subjected to a tare process. With this process, the load values W1, W2, W3, and W4 outputted from the first to fourth load detection means 21a, 21b, 21c, and 21d are respectively set to 0 kgf as the load value applied to each portion of the bed platform 61 in a state in which the object H is not on the bed platform 61.

At Step S1, each load detection means 21a, 21b, 21c, and 21d outputs a voltage corresponding to the load applied to each portion of the bed platform 61. This voltage is transmitted to the control device 22. The transmitted voltage is amplified by the amplification means 22a of the control device 22, converted from an analog signal into a digital signal by the analog-digital conversion means 22b, and then transmitted to the calculation device 30 by the first communication means 23 via a wireless communication network (or a wired communication network). Based on this transmitted voltage, the load value W1, W2, W3, and W4 applied to each portion of the bed platform 61 is calculated by the load value calculation means 31a of the calculation device 30. The voltage and the load value have the relation of the aforementioned Formulas (i) to (iv). Thereafter, the routine proceeds to Step S2.

At Step S2, the total load value A which is a sum of four load values W1, W2, W3, and W4 outputted from the first to fourth load detection means 21a, 21b, 21c, 21d respectively is calculated by the total load value calculation means 31c in a temporally continuous manner (i.e., every predetermined times) [Total Load Value Calculation Step]. The total load value A can be calculated by the aforementioned formula (v). Then, it is judged whether or not the total load value A is, for example, 20 kgf or more as the predetermined load value by the predetermined judgment means (not illustrated) equipped in the judgment portion 33 of the calculation device 30. When it is judged that the total load value A is 20 kgf or more (i.e., A 20 kgf) (in the case of "YES"), the routine proceeds to Step S3. On the other hand, when it is judged that the total load value A is less than 20 kgf (i.e., in the case of A<20 kgf) (in the case of "NO"), the routine returns to Step S2.

In the present invention, the predetermined load value at Step S2 is not limited to 20 kgf. The predetermined load value or more can be, for example, ½ or more of the body weight of the object H, more preferably ¾ or more of the body weight of the object H. The upper limit of the predetermined load value is not limited, and can be set to, for example, the body weight or less of the object H. In the present invention, however, the predetermined load value is not limited to fall within the aforementioned range, and can be changed variously depending on, for example, the body state, the body weight of the object H, etc.

At Step S3, storing of the total load value A in the total load value storage means 32a in a temporally continuous manner will be initiated [Total Load Value Storage Step]. Then, the routine proceeds to Step S4.

At Step S4, it is judged whether or not the total load value A has been maintained the predetermined load value or more for a predetermined time period [Occupancy Judgment Step]. In this embodiment, the predetermined time period is set to, for example, 30 seconds, and the predetermined load value is set to, for example, 20 kgf. When it is judged that the total load value A has maintained the predetermined load value (i.e., 20 kgf) or more for the predetermined time period (i.e., 30 seconds) (in the case of "YES"), the routine proceeds to Step S5. On the other hand, when it is judged contrary (in the case of "NO"), the routine returns to Step S4. In the present invention, the predetermined time period is not limited to 30 seconds, and can be variously changed depending on, for example, the body state, the body weight of the object H, etc. Further, the predetermined load value is not limited to 20 kgf, and can be variously changed depending on, for example, the body state, the body weight of the object H, etc.

At Step S5, the total load value A at the time when the predetermined time period (i.e., 30 seconds) at the occupancy judgment step of Step S4 has passed is stored in the occupancy load value storage means 32b as the load value in the state in which the object H is on the bed platform 61, i.e., the occupancy load value B [Occupancy Load Value Storage Step] In this embodiment, the total load value A at the time when 30 seconds have passed is stored as the occupancy load value B. Then, the routine proceeds to Step S6.

At Step S6, it is judged that the object H has been on the bed platform 61. Next, the routine proceeds to Step S7.

At Step S7, the load value which is a sum of the load value W1 outputted from the first load detection means 21a and the load value W2 outputted from the second load detection means 21 is calculated as a head side load value C in a temporally continuous manner by the head side load value calculation means 31e [Head Side Load Value Calculation Step]. The head side load value C is calculated by the aforementioned formula (vi). Then, storing of the head side load value C calculated by the head side load value calculation means 31e to the head side load value storage means 32c is initiated in a temporally continuous manner [Head Side Load Value Storage Step]. Thereafter, the routine proceeds to Steps S11, S31, S41 and S51.

Figure 5:
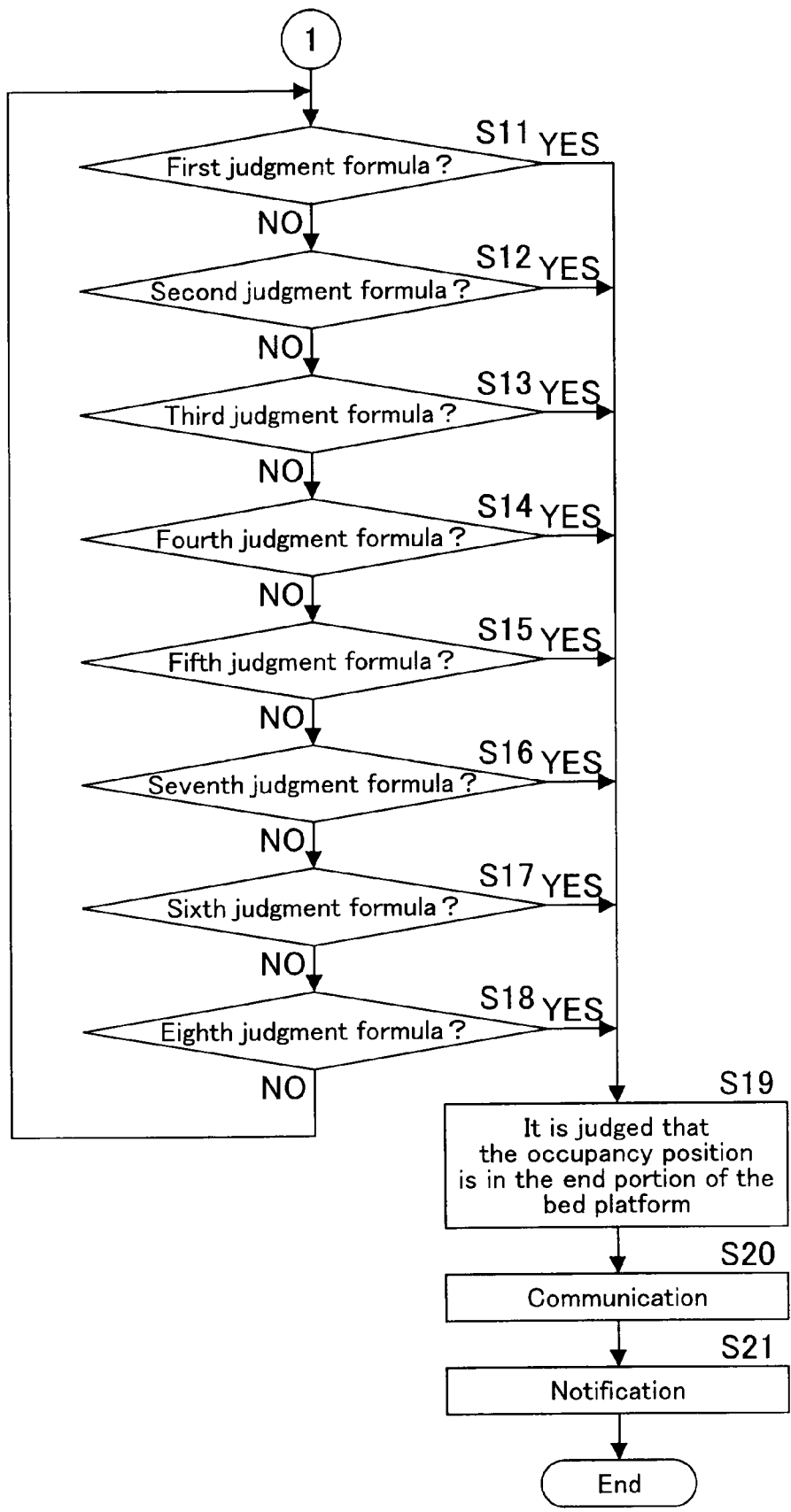
FIG. 5 is a flowchart continued from FIG. 4.

As shown in FIG. 5, at Step S11, it is judged whether or not the aforementioned first judgment formula 1 is satisfied by the first judgment means 33a [First Judgment Step]. In this judgment result, when it is judged that the first judgment formula 1 is satisfied (in the case of "YES"), the routine proceeds to Step S19. On the other hand, when it is judged that the f irst judgment formula 1 is not satisfied (in the case of "NO"), the routine proceeds to Step S11.

At Step S12, it is judged whether or not the aforementioned second judgment formula 2 is satisfied by the second judgment means 33b [Second Judgment Step]. In this judgment result, when it is judged that the second judgment formula 2 is satisfied (in the case of "YES"), the routine proceeds to Step S19. On the other hand, when it is judged that the second judgment formula 2 is not satisfied (in the case of "NO"), the routine proceeds to Step S13.

At Step S13, it is judged whether or not the aforementioned third judgment formula 3 is satisfied by the third judgment means 33c [Third Judgment Step]. In this judgment result, when it is judged that the third judgment formula 3 is satisfied (in the case of "YES"), the routine proceeds to Step S19. On the other hand, when it is judged that the third judgment formula 3 is not satisfied (in the case of "NO"), the routine proceeds to Step S14.

At Step S14, it is judged whether or not the aforementioned fourth judgment formula 4 is satisfied by the fourth judgment means 33d [Fourth Judgment Step]. In this judgment result, when it is judged that the fourth judgment formula 4 is satisfied (in the case of "YES"), the routine proceeds to Step S19. On the other hand, when it is judged that the fourth judgment formula 4 is not satisfied (in the case of "NO"), the routine proceeds to Step S15.

At Step S15, it is judged whether or not the aforementioned fifth judgment formula 5 is satisfied by the fifth judgment means 33e [Fifth Judgment Step]. In this judgment result, when it is judged that the fifth judgment formula 5 is satisfied (in the case of "YES"), the routine proceeds to Step S19. On the other hand, when it is judged that the fifth judgment formula 5 is not satisfied (in the case of "NO"), the routine proceeds to Step S16.

At Step S16, it is judged whether or not the aforementioned sixth judgment formula 6 is satisfied by the sixth judgment means 33f [Sixth Judgment Step]. In this judgment result, when it is judged that the sixth judgment formula 6 is satisfied (in the case of "YES"), the routine proceeds to Step S19. On the other hand, when it is judged that the sixth judgment formula 6 is not satisfied (in the case of "NO"), the routine proceeds to Step S17.

At Step S17, it is judged whether or not the aforementioned seventh judgment formula 7 is satisfied by the seventh judgment means 33g [Seventh Judgment Step]. In this judgment result, when it is judged that the seventh judgment formula 7 is satisfied (in the case of "YES"), the routine proceeds to Step S19. On the other hand, when it is judged that the seventh judgment formula 7 is not satisfied (in the case of "NO"), the routine proceeds to Step S18.

At Step S18, it is judged whether or not the aforementioned eighth judgment formula 8 is satisfied by the eighth judgment means 33h [Eighth Judgment Step]. In this judgment result, when it is judged that the eighth judgment formula 8 is satisfied (in the case of "YES"), the routine proceeds to Step S19. On the other hand, when it is judged that the eighth judgment formula 8 is not satisfied (in the case of "NO"), the routine returns to Step S11.

At Step S19, regarding the information on the bed occupancy state of the object H, it is judged that the occupancy position of the object H is in the end region of the bed platform 61. Thereafter, the routine proceeds to Step S20.

At Step S20, regarding the information on the bed occupancy state of the object H, the information that the occupancy position of the object H is in the end region of the bed platform 61 is transmitted by the first communication means 40a to the first notification means 50a via a wireless communication network or a wired communication network [First Communication Step]. Thereafter, the routine proceeds to Step S21.

At Step S21, regarding the information on the bed occupancy state of the object H, the information that the occupancy position of the object H is in the end region of the bed platform 61 is notified to a nurse, a care personnel, a monitoring personnel, etc., by the first notification means 50a [First Notification Step]. With this notification, the nurse, etc., can obtain the information that the occupancy position of the object H is in the end region of the bed platform 61. With this, for example, the nurse, etc., who obtained this information can take necessary actions to the object H. Actions to the object H include an action for preventing the object H from falling down from the bed platform 61 and an action for assisting the object H who is getting off the bed.

Figure 6:
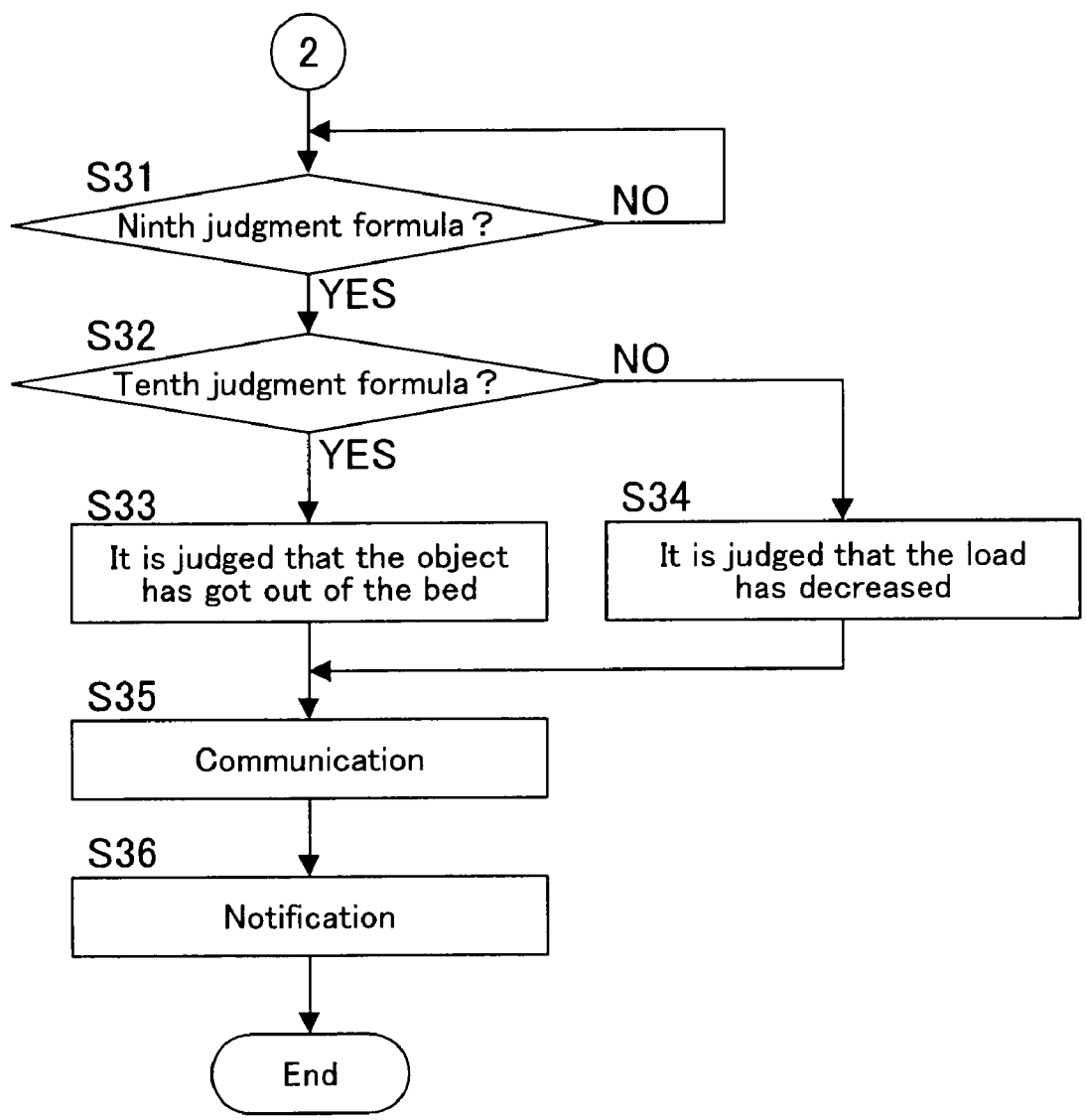
FIG. 6 is a flowchart continued from FIG. 4.

As shown in FIG. 6, at Step S31, it is judged whether or not the aforementioned ninth judgment formula 9 is satisfied by the ninth judgment means 33i [Ninth Judgment Step]. In this judgment result, when it is judged that the ninth judgment formula 9 is satisfied (in the case of "YES"), the routine proceeds to Step S32. On the other hand, when it is judged that the ninth j udgment formula 9 is not satisfied (in the case of "NO"), the routine returns to Step S31.

At Step S32, it is judged whether or not the aforementioned tenth judgment formula 10 is satisfied by the tenth judgment means 33j [Tenth Judgment Step]. In this judgment result, when it is judged that the tenth judgment formula 10 is satisfied (in the case of "YES"), the routine proceeds to Step S33. On the other hand, when it is judged that the tenth judgment formula 10 is not satisfied (in the case of "NO"), the routine proceeds to Step S34.

At Step S33, it is judged that the object H has got out of the bed. Then, the routine proceeds to Step S35.

At Step S34, it is judged that the total load value A (total load) has decreased. At this Step S34, for example, the posture of the object H, e.g., the object H is sitting upright on the end portion of the bed platform 61 or the like, can be judged.

At Step S35, the information that the object H has got out of the bed or the information that the total load value A has decreased is transmitted to the second notification means 50b by the second communication means 40b via a wireless communication network or a wired communication network [Second Communication Step]. Thereafter, the routine proceeds to Step S36.

At Step S36, the information that the object H has got out of the bed or the information that the total load value A has decreased is notified to a nurse, a care personnel, a monitoring personnel, etc., by the second notification means 50b [Second Notification Step]. The nurse, etc. is therefore able to know the information that the object H has got out of the bed or that the total load value A has decreased. With this notification, the nurse, etc., obtained the information can take necessary actions to the object H. Actions to the object H include, for example, assisting of the object H who got out of the bed.

Figure 7:
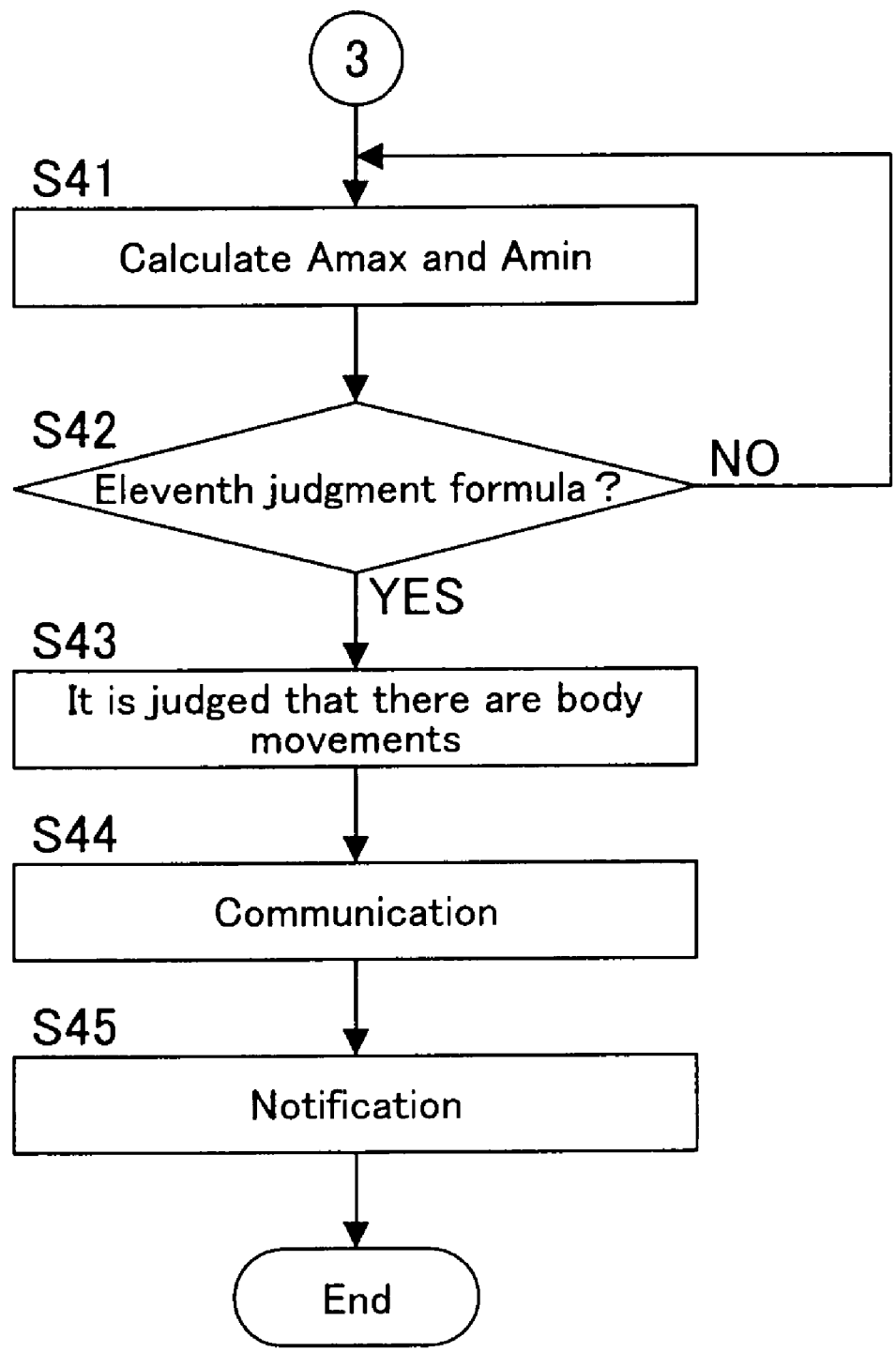
FIG. 7 is a flowchart continued from FIG. 4.

As shown in FIG. 7, at Step S41, the maximum total load value Amax and the minimum total load value Amin of the total load value A calculated by the total load value calculation means 31c within the predetermined time period (e.g., 3 seconds) is calculated by the maximum and minimum load value calculation means 31d in a temporally continuous manner [Maximum and Minimum Load Value Calculation Step]. Thereafter, the routine proceeds to Step S42.

At Step S42, it is judged whether or not the aforementioned eleventh judgment formula 11 is satisfied by the eleventh judgment means 33k [Eleventh Judgment Step]. In this judgment result, when it is judged that the eleventh judgment formula 11 is satisfied (in the case of "YES"), the routine proceeds to Step S43. On the other hand, when it is judged that the eleventh judgment formula 11 is not satisfied (in the case of "NO"), the routine returns to Step S41.

At Step S43, it is judged that there are body movements of the object H. Thereafter, the routine proceeds to Step S44.

At Step S44, regarding the information on the body movements of the object H, the information that there are body movements of the object H is transmitted to the third notification means 50c by the third communication means 40c via a wireless communication network or a wired communication network [Third Communication Step]. Thereafter, the routine proceeds to Step S45.

At Step S45, regarding the body movements of the object H, the information that there are body movements of the object H is notified to a nurse, a care personnel, a monitoring personnel, etc., by the third notification means 50c [Third Notification Step].

Figure 8:
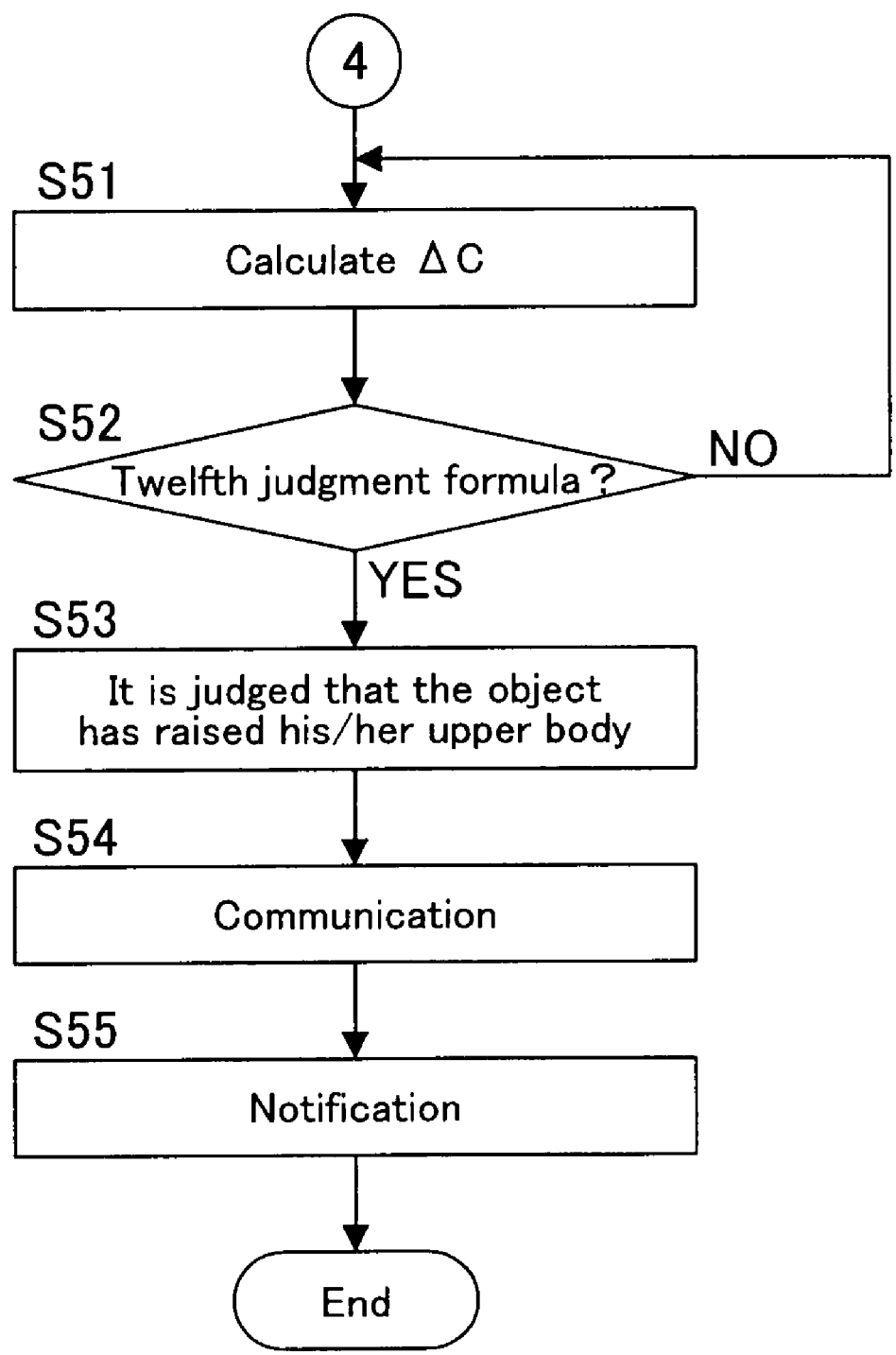
FIG. 8 is a flowchart continued from FIG. 4.

As shown in FIG. 8, at Step S51, the decreased amount $\Delta C$ of the head side load value C calculated by the head side load value calculation means 31e within a predetermined time period (e.g., 3 seconds) is calculated by the head side load value decreased amount calculation means 21f in a temporally continuous manner [Heat Side Load Value Decreased Amount Calculation Step]. Thereafter, the routine proceeds to Step S52.

At Step S52, it is judged whether or not the aforementioned twelfth judgment formula 12 is satisfied by the twelfth judgment means 33l [Twelfth Judgment step]. In this judgment result, when it is judged that the twelfth judgment formula 12 is satisfied (in the case of "YES"), the routine proceeds to Step S53. On the other hand, when it is judged that the twelfth judgment formula 12 is not satisfied (in the case of "NO"), the routine returns to Step S51.

At Step S53, it is judged that the object H has raised his/her upper body. Thereafter, the routine proceeds to Step S54.

At Step S54, the information that the object H has raised his/her upper body is transmitted to the fourth notification means 50d by the fourth communication means 40d via a wireless communication network or a wired communication network [Fourth Communication Step]. Thereafter, the routine proceeds to Step S55.

At Step S55, the information that the object H has raised his/her upper body is notified to a nurse, a care personnel, a monitoring personnel, etc., by the fourth notification means 50d [FourthNotificationStep]. With this information, the nurse, etc., can recognize that the object H has raised his/her upper body.

Thus, the bed occupancy state detection method according to this embodiment has the following advantages.

The bed occupancy state detection method according to this embodiment has the first to eighth judgment steps, and therefore can detect values corresponding to various lying postures of the object H (see the following Evaluation Examples 1 to 3).

Furthermore, each judgment formula (1 to 12) for each judgment step does not include the length and width of the bed platform 61. Therefore, the judgment can be performed not using the length and the width of the bed platform 61, i.e., the size of the bed platform 61. As a result, for example, in performing the detection of the bed occupancy state of the object H, it is not required to previously set the size (length, width, etc.) of the bed platform 61. This enables easy detection of the bed occupancy state of the object H regardless of the bed size.

Furthermore, this detection method includes the first notification step. This enables notification of the information on the bed occupancy state of the object H to a nurse, a care personnel, a monitoring personnel, etc.

Furthermore, this detection method includes the first communication step. This enables transmission of the information on the bed occupancy state of the object H.

In this detection method, the information on the bed occupancy state of the object H is information that the occupancy position of the object H is in the end region of the bed platform 61. This enables notification or transmission of the information that the occupancy position of the object H is in the end region of the bed platform 61.

This detection method includes the ninth judgment step and the tenth judgment step. Thus, it is possible to judge whether or not the object H has got out of the bed as the information on the occupancy status of the object H.

Furthermore, this detection method includes the second notification step. Therefore, the information that the object H has got out of the bed can be notified to a nurse, a care personnel, a monitoring personnel, etc.

Furthermore, this detection method includes the second communication step. Therefore, the information that the object H has got out of the bed can be transmitted.

Furthermore, this detection method includes the eleventh judgment step. Therefore, regarding the information on the bed occupancy state of the object H, it is possible to judge whether or not there are body movements of the object H.

Furthermore, this detection method includes the third notification step. Therefore, the information on the body movements of the object H can be notified to a nurse, a care personnel, a monitoring personnel, etc.

Furthermore, this detection method includes the third communication step. Therefore, the information on the body movements of the object H can be transmitted.

Furthermore, this detection method includes the twelfth judgment step. Therefore, regarding the information on the bed occupancy state of the object H, it is possible to judge whether or not the object H has raised his/her upper body.

Furthermore, this detection method includes the fourth notification step. Therefore, the information that the object H has raised his/her upper body can be notified to a nurse, a care personnel, a monitoring personnel, etc.

Furthermore, this detection method includes the fourth communication step. Therefore, the information that the object H has raised his/her upper body can be transmitted.

The bed occupancy state detection apparatus 20 according to this embodiment has the same advantages as those of the aforementioned detection method.

The bed occupancy state monitoring system 70 according to one embodiment of the present invention is equipped with the aforementioned detection apparatus 20 of this embodiment. Therefore, this monitoring system 70 can assuredly monitor the bed occupancy state of the object H.

Although one embodiment of the present invention was explained, the present invention is not limited to the aforementioned embodiment and can be variously modified.

For example, the bed occupancy state detection device of the present invention can be configured to enable the measurement of the biological information (for example, respiratory rate, heart rate) of the object H in addition to the detection of the bed occupancy state of the object H. Furthermore, the detection device can be combined with a device for measuring the biological information of the object H.

Furthermore, in the aforementioned embodiment, W1, W2, W3, and W4 are values after the tare process. In the present invention, however, W1, W2, W3, and W4 can be values before the tare process, i.e., values including the load of the bed 60 as a tare.

EXAMPLES

Next, concrete Evaluation Examples of the present invention will be shown as follows.

Figure 9:
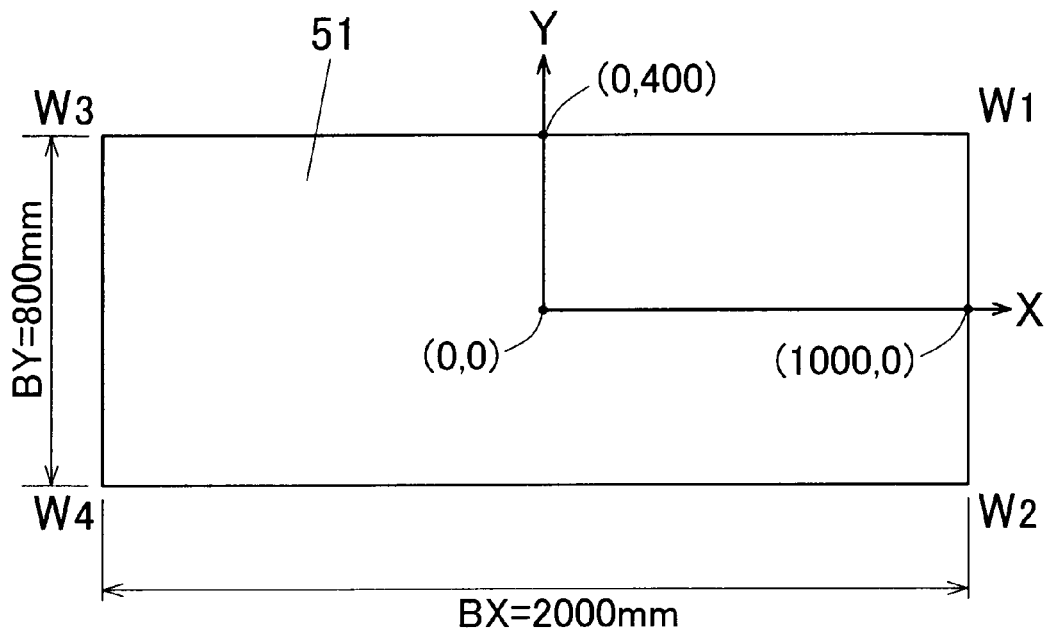
FIG. 9 is a plan view of a bed platform showing the coordinate of the bed platform.

As shown in FIG. 9, a bed 60 in which the longitudinal distance BX between the legs of the bed platform 61 is 2,000 mm and the widthwise distance BY between the legs of the bed platform 61 is 800 mm was prepared. The length direction of the bed platform 61 was set to the X-axis direction, and the widthwise direction of the bed platform 61 was set to Y-axis direction. The body weight of the object H was 100 kgf.

The region covering from the right side edge of the bed platform 61 to the ¼ of BY toward the widthwise central portion of the bed platform 61 was defined as a right end region of the bed platform 61, and the region covering from the left side edge of the bed platform 61 to the ¼ of BY toward the widthwise central portion of the bed platform 61 was defined as a left end region of the bed platform 61. Here, BY was 800 mm. Therefore, the right end region of the bed platform 61 was the widthwise region of 200 mm covering from the right side edge of the bed platform 61 toward the widthwise central portion of the bed platform 61, and the left end region of the bed platform 61 was the widthwise region of 200 mm covering from the left side edge of the bed platform 61 toward the widthwise central portion of the bed platform 61. In the present invention, however, the end region of the bed platform 61 is not limited to the above region.

Furthermore, in the following Evaluation Examples 1 to 3, "n1" to "n8" used for the judgments were as follows.

First Judgment Formula (1): $n1=0.2$
Second Judgment Formula (2): $n2=0.8$
Third Judgment Formula (3): $n3=0.2$
Forth Judgment Formula (4): $n4=0.8$
Fifth Judgment Formula (5): $n5=0.2$
Sixth Judgment Formula (6): $n6=0.8$
Seventh Judgment Formula (7): $n7=0.2$
Eighth Judgment Formula (8): $n8=0.8$

Evaluation Example 1

Figure 10:
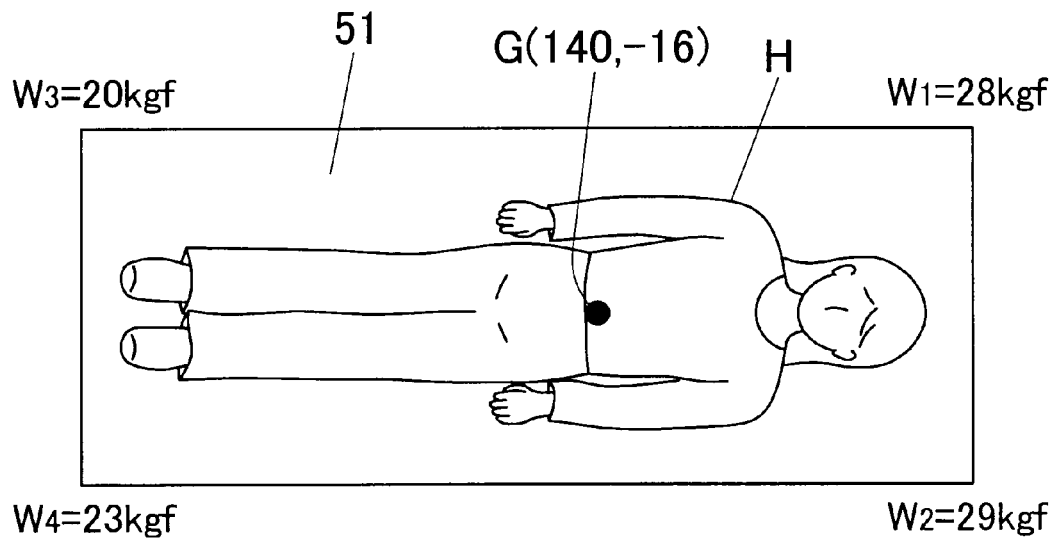
FIG. 10 is a plan view of the bed platform showing the lying posture of an object according to Evaluation Example 1.

As shown in FIG. 10, in the state in which the object H was laying supine on the widthwise central portion of the bed platform 61 along the longitudinal direction of the bed platform 61, W1, W2, W3, and W4 were as follows.
W1=28 kgf
W2=29 kgf
W3=20 kgf
W4=23 kgf In the aforementioned case, the coordinate (GX, GY) of the center of gravity G of the object H was calculated. In other words, the coordinate of the center of gravity G was calculated by the aforementioned Formulas (101) and (102). The result was as follows.
GX=140 mm
GY=−16 mm Therefore, the center of gravity G of the object H was almost in the central region of the bed platform 61.

On the other hand, in the aforementioned case, it was judged whether or not each judgment formula 1 to 8 was satisfied. As a result, none of the judgment formulas were satisfied.

Evaluation Example 2

Figure 11:
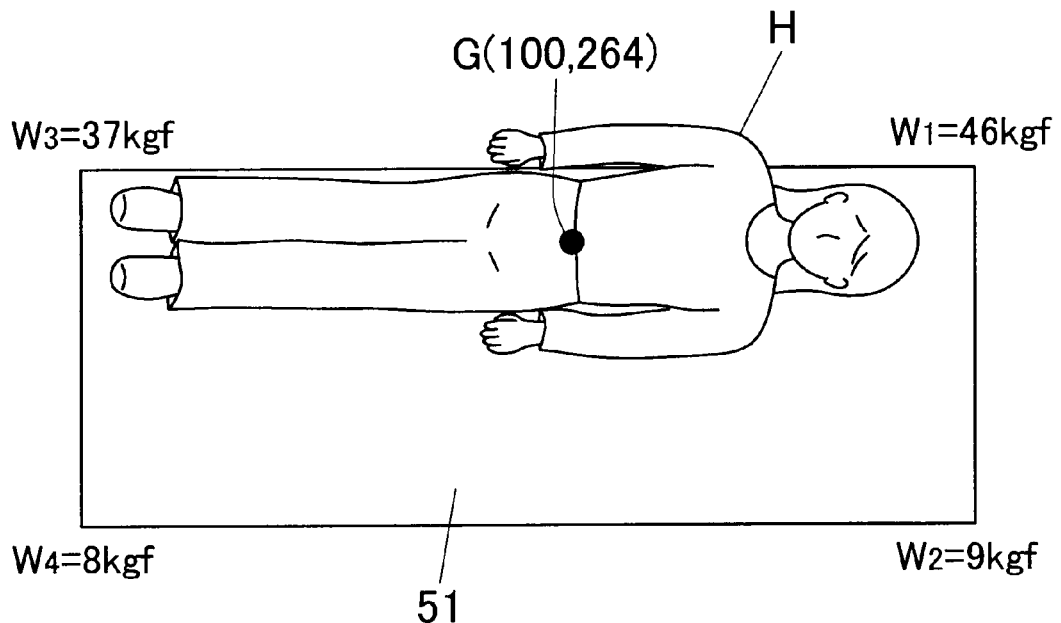
FIG. 11 is a plan view of the bed platform showing the lying posture of an object according to Evaluation Example 2.

As shown in FIG. 11, in the state in which the object H was laying supine on a right end portion of the bed platform 61 along the longitudinal direction of the bed platform 61, W1, W2, W3, and W4 were as follows.
W1=46 kgf
W2=9 kgf
W3=37 kgf
W4=8 kgf In the aforementioned case, the coordinate (GX, GY) of the center of gravity G of the object H was calculated by a conventional detection method. The result was as follows.
GX=100 mm
GY=264 mm Therefore, the center of gravity G of the object H was in the right end region of the bed platform 61.

On the other hand, in the aforementioned case, it was judged whether or not each judgment formula 1 to 8 was satisfied. As a result, the sixth judgment formula 6 and the seventh judgment formula 7 were satisfied.

Accordingly, in cases where the object H lying as shown in FIG. 10 was moved in the widthwise direction of the bed platform 61 while keeping the lying posture in parallel to the longitudinal direction of the bed platform 61, either a conventional detection method or the detection method of the present invention can detect that the occupancy position of the object H has reached within the end region of the bed platform 61.

Evaluation Example 3

Figure 12:
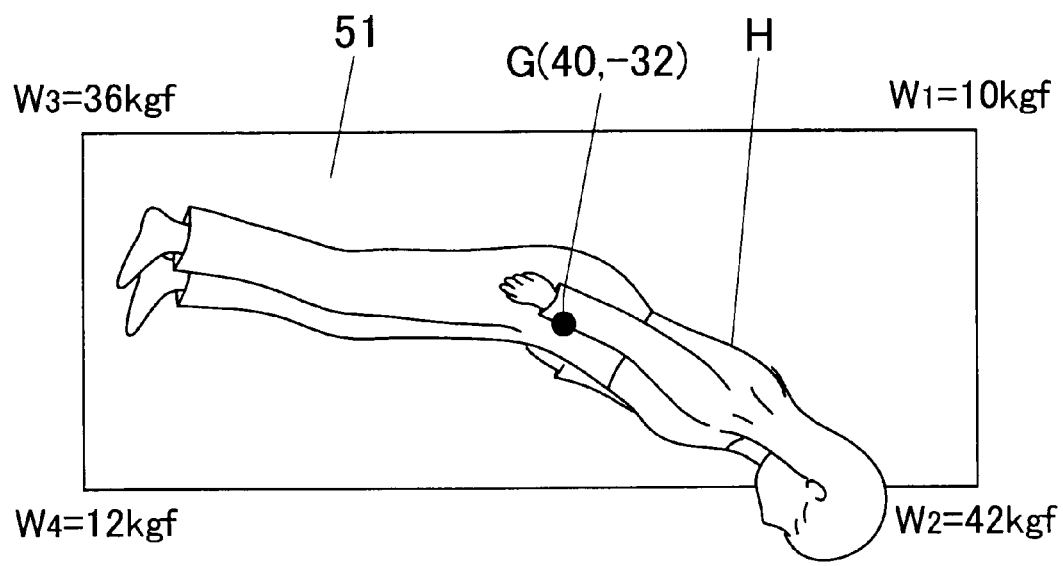
FIG. 12 is a plan view of the bed platform showing the lying posture of an object according to Evaluation Example

As shown in FIG. 12, in the state in which the object H was lying posture with the head portion positioned at the left end portion of the bed platform 61 and the foot portion positioned generally at the widthwise central portion of the bed platform 61, W1, W2, W3, and W4 were as follows. In this lying posture, a part of the head portion of the object H protrudes from the left end portion of the bed platform 61. Therefore, the object H may fall down from the bed platform 61. Further, the object often takes such posture when he or she is going to get out of the bed.

W1=10 kgf
W2=42 kgf
W3=36 kgf
W4=12 kgf

In the aforementioned case, the coordinate (GX, GY) of the center of gravity G of the object H was calculated by a conventional detection method. The result was as follows.

GX=40 mm
GY=−32 mm

Therefore, the center of gravity G of the object H was almost in the central region of the bed platform 61.

On the other hand, in the aforementioned case, it was judged whether or not each judgment formula 1 to 8 was satisfied. As a result, the fifth judgment formula 5 was satisfied.

Therefore, in cases where the lying posture of the object H is in a state as shown in FIG. 12, a conventional detection method cannot detect that the occupancy position of the object H is in the end region of the bed platform 61, but the detection method according to the present invention can detect it.

That is, in cases where the lying posture of the object H is changed from the state shown in FIG. 10 to the state shown in FIG. 12, a conventional detection method cannot detect the change of the lying posture of the object H, but the detection method according to the present invention can detect it. Therefore, according to the detection method of the present invention, it is possible to detect the values corresponding to the lying postures of the object which could not be detected by a conventional detection method, i.e., it is possible to detect the values corresponding to various lying postures of the object.

This application Items priority to Japanese Patent Application No. 2006-168484 filed on Jun. 19, 2006, and the entire disclosure of which is incorporated herein by reference in its entirety.

It should be understood that the terms and expressions used herein are used for explanation and have no intention to be used to construe in a limited manner, do not eliminate any equivalents of features shown and mentioned herein, and allow various modifications falling within the claimed scope of the present invention.

While the present invention may be embodied in many different forms, a number of illustrative embodiments are described herein with the understanding that the present disclosure is to be considered as providing examples of the principles of the invention and such examples are not intended to limit the invention to preferred embodiments described herein and/or illustrated herein.

While illustrative embodiments of the invention have been described herein, the present invention is not limited to the various preferred embodiments described herein, but includes any and all embodiments having equivalent elements, modifications, omissions, combinations (e.g., of aspects across various embodiments), adaptations and/or alterations as would be appreciated by those in the art based on the present disclosure. The limitations in the Items are to be interpreted broadly based on the language employed in the Items and not limited to examples described in the present specification or during the prosecution of the application, which examples are to be construed as non-exclusive. For example, in the present disclosure, the term "preferably" is non-exclusive and means "preferably, but not limited to." In this disclosure and during the prosecution of this application, means-plus-function or step-plus-function limitations will only be employed where for a specific Item limitation all of the following conditions are present in that limitation: a) "means for" or "step for" is expressly recited; b) a corresponding function is expressly recited; and c) structure, material or acts that support that structure are not recited. In this disclosure and during the prosecution of this application, the terminology "present invention" or "invention" may be used as a reference to one or more aspect within the present disclosure. The language present invention or invention should not be improperly interpreted as an identification of criticality, should not be improperly interpreted as applying across all aspects or embodiments (i.e., it should be understood that the present invention has a number of aspects and embodiments), and should not be improperly interpreted as limiting the scope of the application or Items. In this disclosure and during the prosecution of this application, the terminology "embodiment" can be used to describe any aspect, feature, process or step, any combination thereof, and/or any portion thereof, etc. In some examples, various embodiments may include overlapping features. In this disclosure and during the prosecution of this case, the following abbreviated terminology may be employed: "e.g." which means "for example;" and "Ne" which means "note well."

Industrial Applicability

The present invention is applicable to a bed occupancy state detection method, a bed occupancy state detection apparatus, a bed occupancy state monitoring system for detecting, for example, the bed occupancy state (e.g., the values corresponding to the lying postures of an object, a state in which an object is getting out of a bed, a state in which an object is in a bed, the body movements of an object on a bed) of an object on a bed platform.

The invention claimed is:

1. A bed occupancy state detection method, comprising:
a load detection step for detecting loads applied to a head side right portion, a head side left portion, a foot side right portion, and a foot side left portion of a bed platform by first to fourth load detection means, respectively;
wherein load values outputted from the first to fourth load detection means are defined as W1, W2, W3, and W4, respectively,
a first judgment step for judging whether or not a first judgment formula (1) is satisfied, wherein the first judgment formula (1) is given by $W1/(W1+W3) \leq n1$, where $0 < n1 < 0.5$ (n1: previously set value);
a second judgment step for judging whether or not a second judgment formula (2) is satisfied, wherein the second judgment formula (2) is given by $W1/(W1+W3) \geq n2$, where $0.5 < n2 < 1$ (n2: previously set value);
a third judgment step for judging whether or not a third judgment formula (3) is satisfied, wherein the third judgment formula (3) is given by $W2/(W2+W4) \leq n3$, where $0 < n3 < 0.5$ (n3: previously set value);
a fourth judgment step for judging whether or not a fourth judgment formula (4) is satisfied, wherein the fourth judgment formula (4) is given by $W2/(W2+W4) \geq n4$, where $0.5 < n4 < 1$ (n4: previously set value);
a fifth judgment step for judging whether or not a fifth judgment formula (5) is satisfied, wherein the fifth judgment formula (5) is given by $W1/(W1+W2) \leq n5$, where $0 < n5 < 0.5$ (n5: previously set value);
a sixth judgment step for judging whether or not a sixth judgment formula (6) is satisfied, wherein the sixth judgment formula (6) is given by $W1/(W1+W2) \geq n6$, where $0.5 < n6 < 1$ (n6: previously set value);

a seventh judgment step for judging whether or not a seventh judgment formula (7) is satisfied, wherein the seventh judgment formula (7) is given by $W3/(W3+W4) \leq n7$, where $0 < n7 < 0.5$ (n7: previously set value);

an eighth judgment step for judging whether or not an eighth judgment formula (8) is satisfied, wherein the eighth judgment formula (8) is given by $W3/(W3+W4) \geq n8$, where $0.5 < n8 < 1$ (n8: previously set value); and a first notification step for notifying information on a bed occupancy state of an object when it is judged that at least one judgment formula is satisfied from a judgment result of at least one judgment step among the first to eighth judgment steps.

2. The bed occupancy state detection method as recited in claim 1, further comprising a first communication step for transmitting information on the bed occupancy state of the object when it is judged that the judgment formula is satisfied from the judgment result of the at least one judgment step.

3. The bed occupancy state detection method as recited in claim 1, wherein the information on the bed occupancy state of the object is information that an occupancy position of the object is in an end region of the bed platform.

4. The bed occupancy state detection method as recited in claim 1, further comprising:

a total load value calculation step for calculating a total load value A which is a sum of four load values outputted from the first to fourth load detection means;

a total load value storage step for storing the total load value A calculated at the total load value calculation step;

a bed occupancy state judgment step for judging whether or not the object has been on the bed platform depending on whether or not the total load value A calculated at the total load value calculation step has maintained the predetermined load value or more for a predetermined time period;

an occupancy load value storage step of storing the total load value at the time when the predetermined time period has passed as an occupancy load value B in a state in which the object is on the bed platform when it is judged that the object has been on the bed platform from the judgment result of the bed occupancy state judgment step;

a ninth judgment step for judging whether or not a ninth judgment formula (9) is satisfied, wherein the ninth judgment formula (9) is given by $A \leq B \times m1$, where $0 < m1 < 1$ (m1: previously set value); and when it is judged that the ninth judgment formula is satisfied from a judgment result of the ninth judgment step, further comprising, a tenth judgment step for judging whether or not a tenth judgment formula (10) is satisfied, wherein the tenth judgment formula (10) is given by $A < B \times m2$, where $0 < m2 < m1$ (m2: previously set value); and a second notification step for notifying information that the object has got out of the bed when it is judged that the tenth judgment formula is satisfied from the judgment result of the tenth judgment step.

5. The bed occupancy state detection method as recited in claim 4, further comprising a second communicating step for transmitting information that the object has got out of the bed when it is judged that the tenth judgment formula is satisfied from the judgment result of the tenth judgment step.

6. The bed occupancy state detection method as recited in claim 1, further comprising:

a total load value calculation step for calculating a total load value A which is a sum of four load values outputted from the first to fourth load detection means;

a total load value storage step for storing the total load value A calculated at the total load value calculation step;

a bed occupancy state judgment step for judging whether or not the object has been on the bed platform depending on whether or not the total load value A calculated at the total load value calculation step has maintained a predetermined load value or more for a predetermined time period;

an occupancy load value storage step of storing the total load value at the time when the predetermined time period has passed as an occupancy load value B in a state in which the object is on the bed platform when it is judged that the object has been on the bed platform from the judgment result of the bed occupancy state judgment step;

a maximum and minimum load value calculation step for calculating a maximum total load value Amax and a minimum total load value Amin of the total load value A calculated at the total load value calculation step within a predetermined time period;

an eleventh judgment step for judging whether or not an eleventh judgment formula (11) is satisfied, wherein the eleventh judgment formula (11) is given by $Amax - Amin \geq B \times q$, where $0 < q$ (q: previously set value); and a third notification step for notifying information on body movements of the object when it is judged that the eleventh judgment formula is satisfied from the judgment result of the eleventh judgment step.

7. The bed occupancy state detection method as recited in claim 6, further comprising a third communicating step for transmitting information on body movements of the object when it is judged that the eleventh judgment formula is satisfied from the judgment result of the eleventh judgment step.

8. The bed occupancy state detection method as recited in claim 1, further comprising:

a total load value calculation step for calculating a total load value A which is a sum of four load values outputted from the first to fourth load detection means;

a total load value storage step for storing the total load value A calculated at the total load value calculation step;

a bed occupancy state judgment step for judging whether or not the object has been on the bed platform depending on whether or not the total load value A calculated at the total load value calculation step has maintained a predetermined load value or more for a predetermined time period;

a head side load value calculation step for calculating a head side load value C which is a sum of the load value W1 outputted from the first load detection means and the load value W2 outputted from the second load detection means when it is judged that the object has been on the bed platform from the judgment result of the bed occupancy state judgment step;

a head side load value storage step for storing the head side load value C calculated at the head side load value calculation step;

a head side load value decreased amount calculation step for calculating a decreased amount $\Delta C$ of the head side load value C calculated at the head side load value calculation step within a predetermined time period;

a twelfth judgment step for judging whether or not a twelfth judgment formula (12) is satisfied, wherein the twelfth judgment formula (12) is given by $\Delta C \geq A \times s$, where $0 < s$ (s: previously set value); and a fourth notification step for notifying information that the object has raised his/her upper body when it is judged that the twelfth judgment formula is satisfied from the judgment result of the twelfth judgment step.

9. The bed occupancy state detection method as recited in claim 8, further comprising a fourth communicating step for transmitting information that the object has raised his/her upper body when it is judged that the twelfth judgment formula is satisfied from the judgment result of the twelfth judgment step.

10. The bed occupancy state detection method as recited in claim 1, further comprising:

a total load value calculation step for calculating a total load value A which is a sum of four load values outputted from the first to fourth load detection means;

a total load value storage step for storing the total load value A calculated at the total load value calculation step;

a bed occupancy state judgment step for judging whether or not the object has been on the bed platform depending on whether or not the total load value A calculated at the total load value calculation step has maintained a predetermined load value or more for a predetermined time period;

an occupancy load value storage step of storing the total load value at the time when the predetermined time period has passed as an occupancy load value B in a state in which the object is on the bed platform when it is judged that the object has been on the bed platform from the judgment result of the bed occupancy state judgment step;

a ninth judgment step for judging whether or not a ninth judgment formula (9) is satisfied, wherein the ninth judgment formula (9) is given by $A \leq B \times m1$, where $0 < m1 < 1$ (m1: previously set value); and when it is judged that the ninth judgment formula is satisfied from a judgment result of the ninth judgment step, further comprising, a tenth judgment step for judging whether or not a tenth judgment formula (10) is satisfied, wherein the tenth judgment formula (10) is given by $A < B \times m2$, where $0 < m2 < m1$ (m2: previously set value); and a second notification step for notifying information that the object has got out of the bed when it is judged that the tenth judgment formula is satisfied from the judgment result of the tenth judgment step, a maximum and minimum load value calculation step for calculating a maximum total load value Amax and a minimum total load value Amin of the total load value A calculated at the total load value calculation step within a predetermined time period;

an eleventh judgment step for judging whether or not an eleventh judgment formula (11) is satisfied, wherein the eleventh judgment formula (11) is given by $Amax - Amin \geq B \times q$, where $0 < q$ (q: previously set value); and a third notification step for notifying information on body movements of the object when it is judged that the eleventh judgment formula is satisfied from the judgment result of the eleventh judgment step;

a head side load value calculation step for calculating a head side load value C which is a sum of the load value W1 outputted from the first load detection means and the load value W2 outputted from the second load detection means when it is judged that the object has been on the bed platform from the judgment result of the bed occupancy state judgment step;

a head side load value storage step for storing the head side load value C calculated at the head side load value calculation step;

a head side load value decreased amount calculation step for calculating a decreased amount $\Delta C$ of the head side load value C calculated at the head side load value calculation step within a predetermined time period;

a twelfth judgment step for judging whether or not a twelfth judgment formula (12) is satisfied, wherein the twelfth judgment formula (12) is given by $\Delta C \geq A \times s$, where $0 < s$ (s: previously set value); and a fourth notification step for notifying information that the object has raised his/her upper body when it is judged that the twelfth judgment formula is satisfied from the judgment result of the twelfth judgment step.

11. The bed occupancy state detection method as recited in claim 10, further comprising:

a first communication step for transmitting information on the bed occupancy state of the object when it is judged that at least one judgment formula is satisfied from the judgment result of the at least one judgment step among the first to eight judgment steps;

a second communicating step for transmitting information that the object has got out of the bed when it is judged that the tenth judgment formula is satisfied from the judgment result of the tenth judgment step;

a third communicating step for transmitting information on body movements of the object when it is judged that the eleventh judgment formula is satisfied from the judgment result of the eleventh judgment step; and a fourth communicating step for transmitting information that the object has raised his/her upper body when it is judged that the twelfth judgment formula is satisfied from the judgment result of the twelfth judgment step.

12. A bed occupancy state detection apparatus, comprising:

first to fourth load detection means for detecting loads applied to a head side right portion, a head side left portion, a foot side right portion, and a foot side left portion of a bed platforms, respectively;

wherein load values outputted from the first to fourth load detection means are defined as W1, W2, W3, and W4, respectively, first judgment means for judging whether or not a first judgment formula (1) is satisfied, wherein the first judgment formula (1) is given by $W1/(W1+W3) < n1$, where $0 < n1 < 0.5$ (n1: previously set value);

second judgment means for judging whether or not a second judgment formula (2) is satisfied, wherein the second judgment formula (2) is given by $W1/(W1+W3) \geq n2$, where $0.5 < n2 < 1$ (n2: previously set value);

fourth judgment means for judging whether or not a fourth judgment formula (4) is satisfied, wherein the fourth judgment formula (4) is given by $W2/(W2+W4) > n4$, where $0.5 < n4 < 1$ (n4: previously set value);

fifth judgment means for judging whether or not a fifth judgment formula (5) is satisfied, wherein the fifth judgment formula (5) is given by $W1/(W1+W2) < n5$, where $0 < n5 < 0.5$ (n5: previously set value);

sixth judgment means for judging whether or not a sixth judgment formula (6) is satisfied, wherein the sixth judgment formula (6) is given by $W1/(W1+W2) \geq n6$, where $0.5 < n6 < 1$ (n6: previously set value);

seventh judgment means for judging whether or not a seventh judgment formula (7) is satisfied, wherein the seventh judgment formula (7) is given by $W3/(W3+W4) \leqq n7$, where $0<n7<0.5$ (n7: previously set value);

eighth judgment means for judging whether or not an eighth judgment formula (8) is satisfied, wherein the eighth judgment formula (8) is given by $W3/(W3+W4) \geqq n8$, where $0.5<n8<1$ (n8: previously set value); and first notification means for notifying information on a bed occupancy state of an object in cases where it is judged that at least one judgment formula is satisfied from a judgment result of at least one judgment means among the first to eighth judgment means.

13. The bed occupancy state detection apparatus as recited in claim 12, further comprising first communication means for transmitting information on the bed occupancy state of the object when it is judged that the judgment formula is satisfied in the judgment result of the at least one judgment means.

14. The bed occupancy state detection apparatus as recited in claim 12, wherein the information on the bed occupancy state of the object is information that an occupancy position of the object is in an end region of the bed platform.

15. The bed occupancy state detection apparatus as recited in claim 12, further comprising:
    total load value calculation means for calculating a total load value A which is a sum of four load values outputted from the first to fourth load detection means;
    total load value storage means for storing the total load value A calculated by the total load value calculation means;
    bed occupancy state judgment means for judging whether or not the object has been on the bed platform depending on whether or not the total load value A calculated at the total load value calculation means has maintained a predetermined load value or more for a predetermined time period;
    occupancy load value storage means of storing the total load value at the time when the predetermined time has passed as a occupancy load value B in a state in which the object is on the bed platform when it is judged that the object has been on the bed platform from the judgment result of the bed occupancy state judgment means;
    ninth judgment means for judging whether or not a ninth judgment formula (9) is satisfied, wherein the ninth judgment formula (9) is given by $A \leqq B \times m1$, where $0<m1<1$ (m1: previously set value); and
    when it is judged that the ninth judgment formula is satisfied from a judgment result of the ninth judgment means, further comprising,
    tenth judgment means for judging whether or not a tenth judgment formula (10) is satisfied, wherein the tenth judgment formula (10) is given by $A<B \times m2$, where $0<m2<m1$ (m2: previously set value); and
    second notification means for notifying information that the object has got out of the bed when it is judged that the tenth judgment formula is satisfied from the judgment result of the tenth judgment means.

16. The bed occupancy state detection apparatus as recited in claim 15, further comprising second communication means for transmitting information that the object has got out of the bed when it is judged that the tenth judgment formula is satisfied from the judgment result of the tenth judgment means.

17. The bed occupancy state detection apparatus as recited in claim 12, further comprising:
    total load value calculation means for calculating a total load value A which is a sum of four load values outputted from the first to fourth load detection means;
    total load value storage means for storing the total load value A calculated at the total load value calculation means;
    bed occupancy state judgment means for judging whether or not the object has been on the bed platform depending on whether or not the total load value A calculated at the total load value calculation means has maintained a predetermined load value or more for a predetermined time period;
    occupancy load value storage means of storing the total load value at the time when the predetermined time period has passed as an occupancy load value B in a state in which the object is on the bed platform when it is judged that the object has been on the bed platform from the judgment result of the bed occupancy state judgment means;
    maximum and minimum load value calculation means for calculating a maximum total load value Amax and a minimum total load value Amin of the total load value A calculated at the total load value calculation means within a predetermined time period;
    eleventh judgment means for judging whether or not an eleventh judgment formula (11) is satisfied, wherein the eleventh judgment formula (11) is given by $Amax - Amin > B \times q$, where $0<q$ (q: previously set value); and
    third notification means for notifying information on body movements of the object when it is judged that the eleventh judgment formula is satisfied from the judgment result of the eleventh judgment means.

18. The bed occupancy state detection apparatus as recited in claim 17, further comprising third communication means for transmitting information on body movements of the object when it is judged that the eleventh judgment formula is satisfied from the judgment result of the eleventh judgment means.

19. The bed occupancy state detection apparatus as recited in claim 12, further comprising:
    total load value calculation means for calculating a total load value A which is a sum of four load values outputted from the first to fourth load detection means;
    total load value storage means for storing the total load value A calculated at the total load value calculation means;
    bed occupancy state judgment means for judging whether or not the object has been on the bed platform depending on whether or not the total load value A calculated at the total load value calculation means has maintained a predetermined load value or more for a predetermined time period;
    head side load value calculation means for calculating a head side load value C which is a sum of the load value W1 outputted from the first load detection means and the load value W2 outputted from the second load detection means when it is judged that the object has been on the bed platform from the judgment result of the bed occupancy state judgment means;
    head side load value storage means for storing the head side load value C calculated at the head side load value calculation means;
    head side load value decreased amount calculation means for calculating a decreased amount $\Delta C$ of the head side load value C calculated at the head side load value calculation means within a predetermined time period;

twelfth judgment means for judging whether or not a twelfth judgment formula (12) is satisfied, wherein the twelfth judgment formula (12) is given by $\Delta C \geq A \times s$, where $0 < s$ (s: previously set value); and fourth notification means for notifying information that the object has raised his/her upper body when it is judged that the twelfth judgment formula is satisfied from the judgment result of the twelfth judgment means.

20. The bed occupancy state detection apparatus as recited in claim 19, further comprising fourth communication means for transmitting information that the object has raised his/her upper body when it is judged that the twelfth judgment formula is satisfied from the judgment result of the twelfth judgment means.

21. The bed occupancy state detection apparatus as recited in claim 12, further comprising:

total load value calculation means for calculating a total load value A which is a sum of four load values outputted from the first to fourth load detection means;

total load value storage means for storing the total load value A calculated at the total load value calculation means;

bed occupancy state judgment means for judging whether or not the object has been on the bed platform depending on whether or not the total load value A calculated at the total load value calculation means has maintained a predetermined load value or more for a predetermined time period;

occupancy load value storage means of storing the total load value at the time when the predetermined time period has passed as an occupancy load value B in a state in which the object is on the bed platform when it is judged that the object has been on the bed platform from the judgment result of the bed occupancy state judgment means;

ninth judgment means for judging whether or not a ninth judgment formula (9) is satisfied, wherein the ninth judgment formula (9) is given by $A \leq B \times m1$, where $0 < m1 < 1$ (m1: previously set value); and when it is judged that the ninth judgment formula is satisfied from a judgment result of the ninth judgment means, further comprising, tenth judgment means for judging whether or not a tenth judgment formula (10) is satisfied, wherein the tenth judgment formula (10) is given by $A < B \times m2$, where $0 < m2 < m1$ (m2: previously set value); and second notification means for notifying information that the object has got out of the bed when it is judged that the tenth judgment formula is satisfied from the judgment result of the tenth judgment means, maximum and minimum load value calculation means for calculating a maximum total load value Amax and a minimum total load value Amin of the total load value A calculated at the total load value calculation means within a predetermined time period;

eleventh judgment means for judging whether or not an eleventh judgment formula (11) is satisfied, wherein the eleventh judgment formula (11) is given by Amax −Amin $\geq B \times q$, where $0 < q$ (q: previously set value); and third notification means for notifying information on body movements of the object when it is judged that the eleventh judgment formula is satisfied from the judgment result of the eleventh judgment means;

head side load value calculation means for calculating a head side load value C which is a sum of the load value W1 outputted from the first load detection means and the load value W2 outputted from the second load detection means when it is judged that the object has been on the bed platform from the judgment result of the bed occupancy state judgment means;

head side load value storage means for storing the head side load value C calculated at the head side load value calculation means;

head side load value decreased amount calculation means for calculating a decreased amount $\Delta C$ of the head side load value C calculated at the head side load value calculation means within a predetermined time period;

twelfth judgment means for judging whether or not a twelfth judgment formula (12) is satisfied, wherein the twelfth judgment formula (12) is given by $\Delta C \geq A \times s$, where $0 < s$ (s: previously set value); and fourth notification means for notifying information that the object has raised his/her upper body when it is judged that the twelfth judgment formula is satisfied from the judgment result of the twelfth judgment means.

22. The bed occupancy state detection apparatus as recited in claim 21, further comprising:

first communication means for transmitting information on the bed occupancy state of the object when it is judged that at least one judgment formula is satisfied from the judgment result of the at least one judgment means among the first to eight judgment means;

second communication means for transmitting information that the object has got out of the bed when it is judged that the tenth judgment formula is satisfied from the judgment result of the tenth judgment means;

third communication means for transmitting information on body movements of the object when it is judged that the eleventh judgment formula is satisfied from the judgment result of the eleventh judgment means; and fourth communication means for transmitting information that the object has raised his/her upper body when it is judged that the twelfth judgment formula is satisfied from the judgment result of the twelfth judgment means.

23. A bed occupancy state monitoring system, comprising:

first to fourth load detection means for detecting loads applied to a head side right portion, a head side left portion, a foot side right portion, and a foot side left portion of a bed platform, respectively;

wherein load values outputted form the first to fourth load detection means are defined as W1, W2, W3, and W4, respectively, first judgment means for judging whether or not a first judgment formula (1) is satisfied, wherein the first judgment formula (1) is given by $W1/(W1+W3) \leq n1$, where $0 < n1 < 0.5$ (n1: previously set value);

second judgment means for judging whether or not a second judgment formula (2) is satisfied, wherein the second judgment formula (2) is given by $W1/(W1+W3) \geq n2$, where $0.5 < n2 < 1$ (n2: previously set value);

third judgment means for judging whether or not a third judgment formula (3) is satisfied, wherein the third judgment formula (3) is given by $W2/(W2+W4) < n3$, where $0 < n3 < 0.5$ (n3: previously set value);

fourth judgment means for judging whether or not a fourth judgment formula (4) is satisfied, wherein the fourth judgment formula (4) is given by $W2/(W2+W4) \geq n4$, where $0.5 < n4 < 1$ (n4: previously set value);

fifth judgment means for judging whether or not a fifth judgment formula (5) is satisfied, wherein the fifth judgment formula (5) is given by $W1/(W1+W2) \leq n5$, where $0 < n5 < 0.5$ (n5: previously set value);

sixth judgment means for judging whether or not a sixth judgment formula (6) is satisfied, wherein the sixth judgment formula (6) is given by $W1/(W1+W2) \geq n6$, where $0.5 < n6 < 1$ (n6: previously set value);

seventh judgment means for judging whether or not a seventh judgment formula (7) is satisfied, wherein the seventh judgment formula (7) is given by $W3/(W3+W4) \leq n7$, where $0 < n7 < 0.5$ (n7: previously set value);

eighth judgment means for judging whether or not an eighth judgment formula (8) is satisfied, wherein the eighth judgment formula (8) is given by $W3/(W3+W4) \geq n8$, where $0.5 < n8 < 1$ (n8: previously set value); and notification means for notifying information on a bed occupancy state of an object in cases where it is judged that at least one judgment formula is satisfied from a judgment result of at least one judgment means among the first to eighth judgment means.

* * * * *